US011202604B2

(12) United States Patent
Alzamzmi et al.

(10) Patent No.: US 11,202,604 B2
(45) Date of Patent: Dec. 21, 2021

(54) COMPREHENSIVE AND CONTEXT-SENSITIVE NEONATAL PAIN ASSESSMENT SYSTEM AND METHODS USING MULTIPLE MODALITIES

(71) Applicant: University of South Florida, Tampa, FL (US)

(72) Inventors: Ghadh Alzamzmi, North Bethesda, MD (US); Chih-Yun Pai, Tampa, FL (US); Dmitry Goldgof, Lutz, FL (US); Rangachar Kasturi, Tampa, FL (US); Terri Ashmeade, Tampa, FL (US); Yu Sun, Tampa, FL (US)

(73) Assignee: University of South Florida, Tampa, FL (US)

(*) Notice: Subject to any disclaimer, the term of this patent is extended or adjusted under 35 U.S.C. 154(b) by 270 days.

(21) Appl. No.: 16/389,513

(22) Filed: Apr. 19, 2019

(65) Prior Publication Data

US 2019/0320974 A1    Oct. 24, 2019

Related U.S. Application Data

(60) Provisional application No. 62/660,038, filed on Apr. 19, 2018, provisional application No. 62/660,045, (Continued)

(51) Int. Cl.
*A61B 5/00* (2006.01)
*A61B 5/11* (2006.01)
(Continued)

(52) U.S. Cl.
CPC .......... *A61B 5/4824* (2013.01); *A61B 5/0013* (2013.01); *A61B 5/746* (2013.01);
(Continued)

(58) Field of Classification Search
USPC .................................................. 600/300–301
See application file for complete search history.

(56) References Cited

U.S. PATENT DOCUMENTS

| 5,810,392 A | 9/1998 | Gagnon |
| 5,844,488 A | 12/1998 | Musick |

(Continued)

FOREIGN PATENT DOCUMENTS

| CN | 107358180 A | 11/2017 |
| CN | 107392109 A | 11/2017 |

(Continued)

OTHER PUBLICATIONS

International Search Report and Written Opinion issued for International Application No. PCT/US19/28277 dated Jul. 15, 2019.
(Continued)

*Primary Examiner* — Nicole F Lavert
(74) *Attorney, Agent, or Firm* — Smith & Hopen, P.A.; Molly L. Sauter

(57) ABSTRACT

A system and method of automatically assessing pediatric and neonatal pain using facial expressions along with crying sounds, body movement, and vital signs change to improve the diagnosis and treatment of pain in the pediatric patient population.

17 Claims, 6 Drawing Sheets

Related U.S. Application Data filed on Apr. 19, 2018, provisional application No. 62/660,072, filed on Apr. 19, 2018.

(51) Int. Cl.

| | |
|---|---|
| A61B 5/0205 | (2006.01) |
| A61B 5/024 | (2006.01) |
| A61B 5/08 | (2006.01) |
| A61B 5/01 | (2006.01) |
| A61B 5/318 | (2021.01) |

(52) U.S. Cl.
CPC .............. *A61B 5/01* (2013.01); *A61B 5/0205* (2013.01); *A61B 5/02405* (2013.01); *A61B 5/08* (2013.01); *A61B 5/1102* (2013.01); *A61B 5/318* (2021.01); *A61B 2503/045* (2013.01); *A61B 2576/00* (2013.01)

(56) References Cited

U.S. PATENT DOCUMENTS

| | | | |
|---|---|---|---|
| 6,067,019 | A | 5/2000 | Scott |
| 8,764,650 | B2 | 7/2014 | Schiavenato et al. |
| 2006/0128263 | A1 | 6/2006 | Baird |
| 2008/0235030 | A1 | 9/2008 | Sisto et al. |
| 2014/0276188 | A1 | 9/2014 | Jardin |
| 2015/0269424 | A1 | 9/2015 | Bacivarov et al. |
| 2017/0098122 | A1 | 4/2017 | el Kaliouby et al. |
| 2017/0365101 | A1* | 12/2017 | Samec .................... A61B 5/163 |

FOREIGN PATENT DOCUMENTS

| | | |
|---|---|---|
| CN | 107491740 A | 12/2017 |
| JP | 2016186802 A | 10/2016 |
| WO | 2014036263 A1 | 3/2014 |

OTHER PUBLICATIONS

Arif-Rahu et al., "Bio behavioral measures for pain in the pediatric patient." Pain Management Nursing 13.3 (2012): pp. 157-168.
Bagnato et al. "Robust infants face tracking using active appearance models: a mixed-state Condensation approach." Advances in Visual Computing. Springer Berlin Heidelberg, 2007. pp. 13-23.
Beauchemin et al., "The computation of optical flow." ACM Computing Surveys (CSUR) vol. 27, No. 3 (1995): pp. 433 466.
Brahnam et al., "Introduction to neonatal facial pain detection using common and advanced face classification techniques." Advanced Computational Intelligence Paradigms in Healthcare-1. Springer Berlin Heidelberg, 2007. pp. 225-253.
Brahnam, et al., "Machine assessment of neonatal facial expressions of acute pain " Decision Support Systems vol. 43, No. 4 (2007): pp. 1242-1254.
Brahnam et al., "Machine recognition and representation of neonatal facial displays of acute pain." Artificial intelligence in medicine vol. 36, No. 3 (2006): pp. 211-222.
Craig, K.D., et al., Pain in the preterm neonate: behavioural and physiological indices. Pain, 1993. vol. 52, No. (3): pp. 287-299.
Fournier-Charrière et al., "EVENDOL, a new behavioral pain scale for children ages 0 to 7years in the emergency department: Design and validation." PAIN® vol. 153, No. 8 (2012): pp. 1573-1582.
Gholami et al., "Agitation and pain assessment using digital imaging." Engineering in Medicine and Biology Society, 2009. EMBC 2009. Annual International Conference of the IEEE, 2009, pp. 1-13.
Hall et al., "The WEKA data mining software: an update." ACM SIGKDD explorations newsletter vol. 11, No. 1, (2009): pp. 1-10.
Hammal et al., "Automatic detection of pain intensity." Proceedings of the 14th ACM international conference on Multimodal interaction. ACM, 2012, pp. 1-6.
Hicks et al., "The Faces Pain Scale—Revised: toward a common metric in pediatric pain measurement." Pain vol. 93, No. 2 (2001): pp. 173-183.
Holsti et al., Specific Newborn Individualized Developmental Care and Assessment Program movements are associated with acute pain in preterm infants in the neonatal intensive care unit. Pediatrics, 2004. vol. 114, No. 1: pp. 65-72.
Hummel, P.A., et al., Clinical reliability and validity of the N-PASS: neonatal pain, agitation and sedation scale with prolonged pain. Journal of perinatology, 2003. vol. 28, No. 1, pp. 55-60.
Johnston et al., "Experience in a neonatal intensive care unit affects pain response." Pediatrics vol. 98, No. 5 (1996): pp. 925-930.
Kohavi, "A study of cross-validation and bootstrap for accuracy estimation and model selection." IJCAI, vol. 14. No. 2. 1995, pp. 1-8.
Lienhart et al., An Extended Set of Haar-like Features for Rapid Object Detection. IEEE ICIP 2002, vol. 1, pp. 900-903, Sep. 2002.
Lindh et al., "Heel lancing in term new-born infants: an evaluation of pain by frequency domain analysis of heart rate variability." Pain vol. 80, No. 1 (1999): pp. 143-148.
Nanni et al., "A local approach based on a Local Binary Patterns variant texture descriptor for classifying pain states." Expert Systems with Applications vol. 37, No. 12 (2010): pp. 7888-7894.
Saragih et al., "Face alignment through subspace constrained mean-shifts". In International Conference of Computer Vision, Sep. 2009, pp. 1-8.
Shreve et al., "Automatic Expression Spotting in Videos", Image and Vision Computing, vol. 32, No. 8, pp. 476-486, 2014.
Shreve et al., "Macro- and micro- expression spotting in long videos using spatio-temporal strain". International Conference on Automatic Face and Gesture Recognition, pp. 51-56, c 2012 IEEE, Mar. 2011.
Shreve et al., "Towards macro- and micro-expressions spotting in videos using strain patterns". Workshop on Applications of Computer Vision, Dec. 2009, pp. 1-6.
Valeri et al., Pain in preterm infants: Effects of sex, gestational age, and neonatal illness severity. Psychology & Neuroscience vol. 5, No. 1, pp. 11-19.
Viola et al., Rapid Object Detection using a Boosted Cascade of Simple Features. IEEE CVPR, 2001, pp. I-511-I-518.
Viola et al., "Robust real-time face detection." International journal of computer vision vol. 57, No. 2, (2004): pp. 137-154.
Wilson et al., "Facial feature detection using Haar classifiers." Journal of Computing Sciences in Colleges vol. 21, No. 4 (2006): pp. 127-133.
Evans et al.. Longitudinal comparison of preterm pain responses to repeated heelsticks. Pediatric nursing, 2005. vol. 31, No. 3: pp. 216-221.
Fotiadou et al., "Video-based facial discomfort analysis for infants", Proc. SPIE 9029, Visual Information Processing and Communication V, 90290F, 2014, pp. 1-14.
Gibbins, S., et al., Comparison of pain responses in infants of different gestational ages. Neonatology, 2008. vol. 93, No. 1: pp. 10-18.
Hudson-Barr et al., Validation of the pain assessment in neonates (PAIN) scale with the neonatal infant pain scale (NIPS). Neonatal Network. vol. 21, No. 6: pp. 15-21.
Petroni, Marco, et al. "Identification of pain from infant cry vocalizations using artificial neural networks (ANNs)." SPIE's 1995 Symposium on OE/Aerospace Sensing and Dual Use Photonics. International Society for Optics and Photonics, vol. 2492, pp. 729-737.
Brahnam et al., "Neonatal Facial Pain Detection Using NNSOA and LSVM." Ipcv. 2008, pp. 1-7.
Anand, "Consensus statement for the prevention and management of pain in the newborn." Archives of pediatrics & adolescent medicine vol. 155, No. 2, (2001): pp. 173-180.
Allegaert et al., Variability in pain expression characteristics in former preterm infants, J. Perinat. Med. Vol. 33, No. 5, (2005) pp. 442-448.
Hummel et al., N-PASS: Neonatal Pain, Agitation and Sedation Scale—Reliability and Validity, Poster presented at the Pediatric Academic Societies annual meeting, Pediatrics/Neonatology, Loyola University Medical Center, Maywood, IL Perinatal Center, Oncology Institute, vol. 2, N. 6, Nov. 2004, pp. 1-4.

(56) References Cited

OTHER PUBLICATIONS

Lawrence, "The development of a tool to assess neonatal pain." Neonatal network: NN vol. 12, No. 6, (1993): pp. 59-66.

Hazelhoff et al., Behavioral state detection of newborns based on facial expression analysis, International Conference on Advanced Concepts for Intelligent Vision Systems. Springer, Berlin, Heidelberg, 2009.

Holsti et al., Body movements: an important additional factor in discriminating pain from stress in preterm infants, The Clinical journal of pain 2005; 21(6): 491-498.

Lu et al., Facial expression recognition for neonatal pain assessment, 2008 International Conference on Neural Networks and Signal Processing. IEEE, Jun. 8-10, 2008.

\* cited by examiner

400

Communication device 402

Pain monitoring application 404

Input/output application 406

Display 408

Diagnostic application 410

Presentation application 412

Database 414

*FIG. 4*

COMPREHENSIVE AND CONTEXT-SENSITIVE NEONATAL PAIN ASSESSMENT SYSTEM AND METHODS USING MULTIPLE MODALITIES

CROSS-REFERENCE TO RELATED APPLICATIONS

This nonprovisional application claims priority to U.S. Provisional Patent Application No. 62/660,072, entitled "A Comprehensive and Context-Sensitive Neonatal Pain Assessment Using Computer Vision," filed Apr. 19, 2018 by the same inventors. This nonprovisional application claims priority to U.S. Provisional Patent Application No. 62/660,038, entitled "Neonatal Convolutional Neural Network (N-CNN) for Pain Assessment Based on Facial Expression," filed Apr. 19, 2018. This nonprovisional application claims priority to U.S. Provisional Patent Application No. 62/660,045, entitled "System and Method for Recognition of Infants' Pain Based on Facial Expression," filed Apr. 19, 2018. The entirety of each of the foregoing is incorporated herein by these references.

TECHNICAL FIELD

This invention relates to pain assessment. More specifically, the present invention provides a method of assessing the pain of an infant using multiple modalities.

BACKGROUND

The International Association for the Study of Pain (IASP) defined pain as "an unpleasant sensory and emotional experience associated with actual or potential tissue damage or described in terms of such damage." McCaffery [27] described pain as, "whatever the experiencing person says it is, existing whenever the experiencing person says it does." Pain is a stressor and environmental challenge that requires the organism to respond. The reaction to the stimulus can be sensed as temperature, itching, sharpness, aching, throbbing. Pain sensation does not necessarily depend on tissue damage. Pain may be a conditional stimulus that can elicit strong affective response. Pain may be categorized according to various factors including type of damage, duration, and time to heal. Pain may be acute or chronic, where the chronic pain lasts for a longer time than acute pain. Both acute and chronic pain can lead to various issues not simply physiologic or psychologic. Pain can be further categorized as nociceptive and neuropathic pain. Where nociceptive pain includes visceral and somatic pain, while neuropathic pain includes peripheral and central neuropathic pain.

The nociceptive pain is the discomfort experienced as a result of an injury. The injury may include but is not limited to a paper cut, a broken bone, appendicitis and the like. The neuropathic pain is associated with an injury to a nerve or central nervous system. Such injuries can give rise to paresthesias. For example, the paresthesias may include but is not limited to numbness, tingling, electrical sensations and the like. Further, the neuropathic pain can also generate unusual symptoms. For example, the unusual symptoms may include anesthesia dolorosa in which the area producing the pain is numb to touch.

The experience of pain varies from person to person due to inter-individual variability. Moreover, the intensity of pain varies from cause to cause in the individual. Thus, pain management is an extremely important issue. Various factors, directly or indirectly, contribute in controlling the pain. For example, biological factors (for e.g., gender, genetics and the like), psychological factors (for e.g., mood, attention, distraction and the like), social factors (for e.g., marital status, social support and the like) and the like can significantly modulate the intensity as well as unpleasantness caused by the pain. This experience of pain is complicated even further in neonates.

Neonates do not have the ability to communicate this experience verbally (self-evaluation) or nonverbally by writing or pointing (e.g. Visual Analog Scale). The limited ability of neonates to communicate pain as well as the earlier misconceptions—the absence of neurological substrate for the perception of pain in neonates—has led pediatricians to believe, for several decades, that neonates do not feel or remember pain.

Sufficient scientific studies [43], [21], [19], [8], [3], [20], [40], [30], [11], [16] disproved this earlier belief and reported serious short- and long-term outcomes of pain exposure in early life. For example, studies have found that unexpected and repeated painful experiences during early life are associated with alterations in the pain sensitivity and perception [30] (e.g., allodynia and hyperalgesia), stress-response system functioning [21], [43] (e.g., high basal cortisol levels), and postnatal growth [40] (e.g., slower body weight gain and head growth). In addition, there is strong evidence that extensive pain exposure during early life is associated with changes in the brain structure and function, including changes in the cerebral white matter and subcortical grey matter [20], [21], delayed corticospinal development [19], [20], and alterations in the number of synaptic connections and the degree of capillary branching that augments the blood and oxygen supply [8], [3]. These alterations can result in a variety of behavioral, developmental, and learning disabilities [19], [16].

A comprehensive discussion of the short-term outcomes (e.g., increased heart rate, oxidative stress and cortisol) and longterm outcomes (e.g., delayed visual perceptual development, neurodevelopmental impairments, lower IQs, and internalizing behavior) of pain exposure in early life have been explored in the art [16].

The recognition of the adverse effects of neonatal pain has led to recommendations for the increased use of analgesic medications in neonates, including opioids. However, recent studies [9], [4], [23], [48] found that the excessive use of analgesic medications such as Morphine and Fentanyl may cause a variety of side effects. For example, Zwicker et al. [48] found that a 10-fold increase in Morphine, an agent commonly used for neonatal pain management, is associated with impaired cerebellar growth in the neonatal period and poorer neurodevelopmental outcomes in the early childhood period. In addition, recent studies demonstrated that Morphine increases apoptosis in human microglial cells [23] and neuronal like cells in neonatal rats [4]. Studies in neonatal rats have found long term alterations in brain function and structure following exposure to Morphine [9], [4]. The side effects of another well-known analgesic medication (i.e., Fentanyl) were discussed in [16]. This study described Fentanyl as an extremely potent analgesic and listed several side effects (e.g., neuroexcitation and respiratory depression) with high doses of Fentanyl.

These findings suggest that both the failure to recognize and treat neonatal pain (i.e., under treatment) as well as the administration of certain analgesic medications in the absence of pain (i.e., over treatment) may lead to serious outcomes and cause permanent alterations in brain structure and function. These alterations may contribute to the high incidence of neurodevelopmental disability occurring in preterm and hospitalized full-term neonates. The annual cost of care related to adverse neurodevelopmental outcomes in preterm neonates alone is estimated at over 7 billion dollars [12].

Although neonates are incapable of communicating their pain experience, their body responds to painful stimuli in two different ways: behaviorally (e.g., facial expression, dysregulated sleep pattern, crying), physiologically (e.g., changes in nounced release of catecholamines). The intensity and pattern of these responses differ across different types of pain, which are procedural, postoperative, and chronic [2]. The procedural pain is usually associated with a short painful stimulus such as immunization and it ends as soon as the cause of pain is removed. Postoperative pain has a clearly defined beginning and expected end point and it occurs after a known stimulus such as a surgical procedure. Neonates' behavioral responses to the procedural painful stimulus are usually more intense as compared to their response to postoperative pain. This can be attributed to the low physical reserves of a neonate to sustain a response and the level of sedation/analgesia. Finally, neonatal chronic pain is defined as the persistent and ongoing pain that lasts beyond a normal three-month healing time and does not have an expected end point. It has been reported that neonates with chronic pain become hyporeactive over time and that the usefulness of their physiological indicators decreases as the pain continues unabated [2]. There have been other discussions of methods and systems for pain monitoring and management in a pediatric patient as can be seen in U.S. Patent Publication 2016/0262691 to Jain et al, as well as Chinese Patent Applications CN106682616 and CN102663450. However, none of the currently available methods or system is a comprehensive, wholistic, and context-sensitive system.

On average, infants receiving care in the Neonatal Intensive Care Unit (NICU) experience fourteen painful procedures per day [36]. The current practice for assessing neonatal pain involves bedside caregivers observing multiple behavioral (e.g., facial expression and crying) and physiological (e.g., changes in vital signs) responses of pain. This practice of assessment has three main limitations. First, it relies on the caregiver's direct observation and interpretation of multiple responses, including behavioral, and physiological responses.

The caregiver's observation is highly biased and is affected by several idiosyncratic factors, such as the observer's cognitive bias, identity, culture, and gender [35], [28]. Second, caregivers assess pain at different time intervals and are not able to provide continuous assessment. The discontinuity of assessment can lead to missing pain, while the neonate is left unattended, and therefore may result in delayed intervention. Third, this practice involves a substantial time commitment and requires a large number of well-trained caregivers to ensure the proper utilization of the pain scale.

There has been an increasing interest [45] in the past several years to improve the current practice of assessing neonates' pain by developing automated and round-the-clock systems. However, most existing solutions focus on analyzing and assessing adult pain. This can be attributed to the lack of publicly-available neonatal datasets. Another reason is the common belief that the algorithms designed for adults should have similar performance when applied to neonates. Contrary to this belief, however, the methods designed for assessing adults' pain will not have similar performance and might completely fail for two main reasons. The first reason is that the pain dynamics and facial morphology vary between infants and adults as reported in [31]. Moreover, it has been reported that infants' facial expressions include additional movements and units that are not present in the Facial Action Coding System and therefore the Neonatal FACS [31] was introduced as an extension of FACS. Additionally, neonates' sound and body movement during pain have different pattern and dynamics than those of adults. The second reason is that the preprocessing stage (e.g., face and body tracking) is more challenging in the case of neonates since they are uncooperative subjects recorded in a highly unconstrained environment such as the NICU.

In depth discussion and a comprehensive review of the existing methods for neonatal pain recognition can be found in [45].

A. Facial Expression

The existing methods that assess neonatal pain based on analysis of facial expression are divided into static and dynamic methods.

1) Static Methods

The static methods extract pain-relevant features from static images and then use those extracted features to train off-the-shelf machine learning classifiers. The existing static methods for analyzing neonatal facial expression of pain are divided into two main categories, namely Handcrafted-representation-based methods and Deep-representation-based methods, and briefly describe them below.

Handcrafted-representation-based methods are the methods that are manually designed or handcrafted by human experts to extract given set of chosen characteristics. Examples of well-known handcrafted methods include Local Binary Pattern (LBP) and Histogram of Oriented Gradients (HOG).

A handcrafted method to extract pain-relevant features from static images of neonates is presented in [10]. A total of 204 static images (COPE Database) were captured for 26 healthy infants (gender: 50% female, age: 18 hours to 3 days) during the four following stimuli, 1) the puncture of a heel-lance; 2) friction on the external lateral surface of the heel; 3) transport from one crib to another; and 4) an air stimulus to provoke an eye squeeze. The proposed method took a static image as input and concatenates it into a feature vector of $Image_W \times Image_H$ dimensions with values ranging from 0 to 255. Then, Principal Component Analysis (PCA) was applied to reduce the vector's dimensionality. For classification, distance-based classifiers and Support Vector Machines (SVMs) were used to classify the images into one of the following four pair: pain/no-pain, pain/cry, pain/air-puff, and pain/friction. The results showed that SVMs, which were evaluated using 10-fold cross-validation, achieved the best recognition rate and outperformed distance-based classifiers in classifying pain versus no-pain (88.00%), pain versus rest (94.62%), pain versus cry (80.00%), pain versus air-puff (83.33%), and pain versus friction (93.00%).

Another handcrafted-representation-based method is presented in [29]. Several variations of Local Binary Pattern (LBP) (i.e., Local Ternary Pattern (LTP), Elongated Local Binary Pattern (ELBP), and Elongated Local Ternary Pattern (ELTP) were applied to static images of the COPE dataset to extract handcrafted features. The features extracted using ELTP descriptor achieved the highest performance (0.93 AUC) in classifying neonates' images as pain or no-pain images.

Similarly, Mansor et al. [25] presented an LBP-based method that is robust to different level of illuminations. The presented method modified COPE dataset by altering the original images and adding different levels of illuminations. Then, a Multi Scale Retinex (MSR) image filter was applied to remove illumination followed by LBP for feature extraction. The extracted texture features were used to train an unsupervised Gaussian classifier and supervised Nearest Mean classifier. The highest average accuracy (83.00%) of the proposed method was achieved by Gaussian classifier.

Celona and Manoni [13] applied two handcrafted descriptors, namely LBP and the Histogram of Oriented Gradients (HOG), to static images of COPE dataset. The handcrafted feature vectors extracted using LBP and HOG were reduced to 175-dimension (i.e., 175-dimension LBP and 175-dimension HOG) using Principal Component Analysis (PCA) followed by L2 normalization. In the final stage, a feature fusion of the reduced feature vectors was performed to form a single feature vector with 175 L dimension, where L is the number of feature vectors. This method achieved an average accuracy of 81.98%.

Deep features, which are extracted by Convolutional Neural Networks (CNN) at multiple levels of abstraction, have recently been used to recognize facial expressions of pain. For example, Celona and Manoni [13] applied transfer learning method on static images of the COPE dataset to classify these images as pain or no-pain images. In particular, the presented method extracted deep features from pre-trained CNN (VGG-Face) and used these features to build a Support Vector Machine (SVM) model. Testing the trained model on unseen data (i.e., leave-one-subject-out cross validation) achieved 82.42% average accuracy. Combining the deep features extracted from the pre-trained CNN with handcrafted features (LBP) improved the pain classification and achieved an average accuracy of 83.78%.

2) Dynamic Methods

The main limitation of previously presented methods is that they were designed for and tested on static images taken at a specific shot. Because facial expressions are dynamic events that unfold in a particular pattern over time, it is important to take the temporal information into account when developing facial expression recognition methods. Fotiadou et al. [17] proposed a dynamic method to detect pain expression from videos. For each video, Active Appearance Model (AAM) was applied, after detecting the face, to track the facial landmarks through the video frames and extract global motion. SVM classifier, which was evaluated using leave-one-subject-out cross-validation, achieved 0.98 AUC in detecting pain expression.

Zamzmi et al. [47] proposed a motion-based method to recognize neonatal pain expression from videos. The proposed method computes the optical flow between consecutive video frames and use it to estimate the optical strain magnitudes, which measure the facial tissue deformations occurred during facial expressions. Then, a peak detector was applied to the strain curves to find the maximum strain magnitudes (i.e., peaks) that correspond to facial expressions. For classification, the extracted strain features were used to train different machine-learning classifiers, namely SVM and Knearest-neighbors (KNN). To evaluate the trained model and estimate the generalization performance, leave-one-subject-out cross-validation protocol was applied. The obtained average accuracy was around 93.2%.

B. Infant Cry

Several methods were proposed to classify neonatal cry as pain cry or no-pain cry. These methods can be divided into, Time Domain, Frequency Domain, and Cepstral Domain methods.

1) Time Domain Analysis

Time Domain analysis is the analysis of a signal with respect to time (i.e., the variation of a signal's amplitude over time). Example of Time Domain features that are commonly used for infants' sound analysis are energy, amplitude, and pause duration. Vempada et al. [39] presented a Time Domain method to classify neonatal cry as pain, hunger, or wet-diaper. In the feature extraction stage, two features were calculated: 1) Short Time Energy (STE), which is the average of the square of the sample values in a suitable window; and 2) pause duration within the crying segment. Part of these features were used to build SVM and the remaining were used to evaluate its performance. The recognition performance of pain cry, hunger cry, and wet-diaper cry were 83.33%, 27.78%, and 61.11% respectively.

2) Frequency Domain Analysis

Frequency Domain analysis shows the distribution of the signal within a specific range of frequencies. Examples of common Frequency Domain features include the fundamental frequency (F0) and the first three formants (i.e., F1, F2, and F3).

Pal et al. [33] used the Harmonic Product Spectrum (HPS) method to extract the Fundamental Frequency (F0) method along with the first three formants (i.e., F1, F2, and F3) from crying signals of infants recorded during several emotional states (i.e., pain, hunger, fear, sadness, and anger). After extracting the features, k-means algorithm was applied to find the optimal parameters that maximizes the separation between features of different types of cry. Combining F0, F1 and F2 produced the best clustering and achieved an accuracy of 91% for pain, 72% for hunger, 71% for fear, 79% for sadness, and 58% for anger. Another Frequency Domain method for analyzing neonatal cry during pain is presented in [18].

3) Cepstral Domain Analysis

The Cepstral Domain of a signal is generated by taking the Inverse Fourier Transform (IFT) of the logarithm of the signal's spectrum. Mel Frequency Cepstral Coefficients (MFCC) is a common Cepstral Domain method that is used to extract a useful and representative set of features (i.e., coefficients) from a sound signal and discard noise and non-useful features.

One of the first studies to analyze neonatal crying episodes using MFCC was introduced in [26]. The proposed method was applied to a dataset that consists of 230 crying episodes collected from 16 healthy neonates (2 to 6 months old). The crying episodes (pain), jack-in-the-box (fear), and head restraint (anger). The crying signals of fear and anger were combined together to represent crying episodes not related to pain. Prior to the feature extraction stage, all episodes were filtered to 8000 Hz using a low-pass filter, sampled at 16 kHz, and segmented into 256-sample frames (16 ms) with 50% overlapping. For each segment, 10 MFCCs were extracted and fed into a neural network as input. The testing protocol was 10-fold cross validation. The highest correct classification rates for pain and no pain classes were 92.0% and 75.7% respectively. Other Cepstral domain methods for analyzing neonatal crying episodes while undergoing a painful procedure can be found in [6], [1].

C. Body Movement

Neonates tend to move their head, extend their arms, kick their legs, and splay their fingers when they experience pain. There are no known methods for neonatal pain assessment based on analysis of body movement, and thus no known methods that include analysis of body movement in a larger system and method for assessing pain.

D. Vital Signs Readings

Several studies [15], [37] investigated the association between changes in vital signs and neonatal pain. Although studies have found a correlation between changes in vital signs and pain, vital sign changes can be associated with other emotions not related to pain (e.g., hunger and fear) or underlying illness [7]. Therefore, it has been suggested [7] to use vital signs in conjunction with behavioral responses, which are considered more pain-specific, for pain assessment.

E. Contextual Data

Pediatric studies [14], [28], [38] reported strong associations between medical and contextual data (e.g., gestational age and oral sucrose) and neonates' response to pain. For example, it has been reported that neonates with very low gestational age have poor regulation of central nervous system development, and hence have limited ability to behaviorally communicate pain in comparison to full-term neonates [38]. In addition, a previous study [14] found that adult females have higher behavioral pain responses than males, while the physiological pain responses (i.e., hemodynamic response of the brain) for male neonates were found to be more pronounced than female neonates [14]. Differences in reaction to pain based on weight have also been reported in the literature [38]. Due to these findings, we believe that incorporating medical and contextual data with other pain responses is necessary to refine the assessment process and obtain a context-sensitive assessment.

There is a need in the art for a system and method that effectively and efficiently combines these pain responses together for the purpose of assessing neonatal pain.

While certain aspects of conventional technologies have been discussed to facilitate disclosure of the instant application, Applicants in no way disclaim these technical aspects, and it is contemplated that the instant application may encompass one or more of the conventional technical aspects discussed herein.

The present disclosure may address one or more of the problems and deficiencies in the art discussed above. However, it is contemplated that this disclosure may prove useful in addressing other problems and deficiencies in many technical areas. Therefore, the present application should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

This summary is provided to introduce a selection of concepts in a simplified form. These concepts are described in further detail in the detailed description of example embodiments of the disclosure below. This summary is not intended to identify key features or essential features of the claimed subject matter, nor is it intended to be used to limit the scope of the claimed subject matter.

The inventors propose a non-invasive and comprehensive system that simultaneously measures the traditionally observed behavioral and physiological pain responses and utilizes them to assess neonatal pain. This disclosure describes the combination of facial expression, crying sound, body movement, and vital signs readings using feature fusion and decision fusion methods to create a multimodal assessment.

Infants receiving care in the Neonatal Intensive Care Unit (NICU) experience several painful procedures during their hospitalization. Assessing neonatal pain is difficult because the current standard for assessment is subjective, inconsistent, and discontinuous. The intermittent and inconsistent assessment can induce poor treatment and, therefore, cause serious longterm outcomes. The present application is a comprehensive pain assessment system that utilizes facial expressions along with crying sounds, body movement, vital signs changes, and contextual data. This is the first system and method that includes patient body movement. The proposed automatic system generates continuous and standardized pain assessment comparable to those obtained by conventional nurse-derived pain scores. The system achieved 90% and 94% accuracies using feature fusion and decision fusion of different pain responses that were recorded in a challenging clinical environment. In addition, we propose several group-specific models for pain assessment, for example pre-term and full-term models, since pediatric studies have reported different pain responses for different groups of neonates. The results show that the automatic assessment of neonatal pain is a viable and more efficient alternative to the manual assessment.

Embodiments disclosed herein include a pain assessment system to monitor the intensity of pain experienced by a patient. For example, in accordance with one embodiment the pain assessment system includes: a communication device, which itself includes, control circuitry; data store; input/output circuitry; communication circuitry; a pain monitoring application. The pain monitoring application includes: an input/output application which gathers data from a camera. The camera captures facial expressions of a patient along with sounds, and body movement. The system also includes a medical device to gather physiological data from the patient through a plurality of bio-sensors. The system includes a contextual data gathering device, which stores a pain monitoring scale data point, and contextual data of the patient. Further, the system includes a display application to display the data gathered from the input/output application. The system also includes a diagnostic application to assess the data gathered from the input/output application. The system includes a presentation application to generate a pain profile for the patient; and a database to store the data gathered from the input/output application, the display application, the diagnostic application, and the presentation application.

In an embodiment, the pain assessment system contains a diagnostic application which provides automated comparison of the real-time data from the input/output application and the database to provide pain intensity measurements for the patient.

In an embodiment, the pain assessment system includes a plurality of bio-sensors attached to various points on a body of the patient.

In an embodiment, the plurality of bio-sensors includes a finger-based pulse oximeter, an accelerometer, a respiration monitor and a 1-lead disposable electrocardiography (ECG) patch or a multiple lead ECG, an electroencephalography (EEG) sensor, or a muscle activity sensor.

In an embodiment, the physiological data gathered by the system includes one or more of heart rate (HR), heart rate variability (HRV), skin conductance, respiration information, blood pressure, photoplethysmography (PPG), oxygen saturation, single or multiple lead electrocardiography (ECG), electroencephalography (EEG), muscle activity (EMG), galvanic skin response (GSR), skin conductance, pulse wave transit time, atrial kick, BCG (Balistocardiogram), EOG (Electrooculography), Dispersion based ECG, Impedence cardiography, VO2 max, PaCO2, facial features, stress, emotion detectors, cardiac output, oxygen saturation, blood glucose, blood gas, temperature, sweat, hydration, gaze, movements, and restlessness.

In an embodiment, the pain monitoring scale data point is selected from: a visual analog scale (VAS), a verbal numerical rating scale (VNRS), a brief pain inventory (BPI), verbal descriptor scale (VDS), a neonatal pain agitation and sedation scale (N-PASS), a pain assessment tool (PAT), a bernese pain scale for one or more neonates (BPSN), Neonatal Infant Pain Scale (NIPS), wong-baker scale, a face, legs, activity, crying, and consolability (FLACC) scale.

In an embodiment, the contextual data gathering device collects phenotypical, genotypical, and mental attributes of the patient.

In an embodiment, the contextual data gathering device collects data including biological factors (gender, genetics and the like), psychological factors (mood, attention and the like), experimental factors, duration of measurement of the intensity of the pain and location of each sensor of the plurality of bio-sensors on the body of each of the one or more patients.

In an embodiment, the camera captures facial expressions of a patient along with sounds, and body movement at recorded time period intervals of five, ten, and fifteen seconds. In addition, ZFace or any equivalent tracker. is applied to the facial expressions to obtain facial landmark points and face boundary points.

In an embodiment, the facial expressions are extracted with strain-based and geometric-based extraction to extract pain-relevant features from the patient.

In an embodiment, the camera captures audio data that is segmented into audio signal and divided into several Hamming windows of 32-millisecond that shifts every 16-millisecond and Hamming windows of 30-millisecond that shifts every 10-millisecond to minimize the signal discontinuities.

In an embodiment, the physiological data is processed with median filter to calculate several descriptive statistics for the physiological data across the pain or no pain event.

In an additional embodiment, a method to monitor the intensity of pain experienced by a patient. The method includes: providing a communication device, which includes a control circuitry; a data store; input/output circuitry; communication circuitry; a pain monitoring application. The pain monitoring application includes: an input/output application; a display application to display the data gathered from the input/output application; a diagnostic application to assess the data gathered from the input/output application; a presentation application to generate a pain profile for the patient; and a database. The database stores the data gathered from the input/output application, the display application, the diagnostic application, and the presentation application. The method includes gathering data through the input/output application from: a camera, which captures facial expressions of a patient along with sounds, and body movement; a medical device to gather physiological data from the patient through a plurality of bio-sensors; and a contextual data gathering device. The contextual data gathering device stores a pain monitoring scale data point, and contextual data of the patient. The method includes assessing the intensity of the pain of the patient in the diagnostic application by automatically processing the data from the input/output application; and delivering the pain profile of the patient through the presentation application.

In an embodiment, the facial expression data is used to train a machine learning classifier.

In an embodiment, the machine learning classifier is selected from the group consisting of: Naïve Bayes, Nearest Neighbors (kNN), Support Vector Machines (SVMs), and Random Forests (RF) classifiers.

In an embodiment, the method for assessing the intensity of the pain experienced by the patient is either a feature-level method or a decision-level method.

BRIEF DESCRIPTION OF THE DRAWINGS

While the specification concludes with claims particularly pointing out and distinctly claiming what are regarded as embodiments of the invention, the advantages of embodiments of the disclosure may be more readily ascertained from the description of certain examples of embodiments of the disclosure when read in conjunction with the accompanying drawings, in which:

FIG. 4 depicts a system showing a block diagram of a communication device, in accordance with various embodiments of the present disclosure.

DETAILED DESCRIPTION

Figure 1:
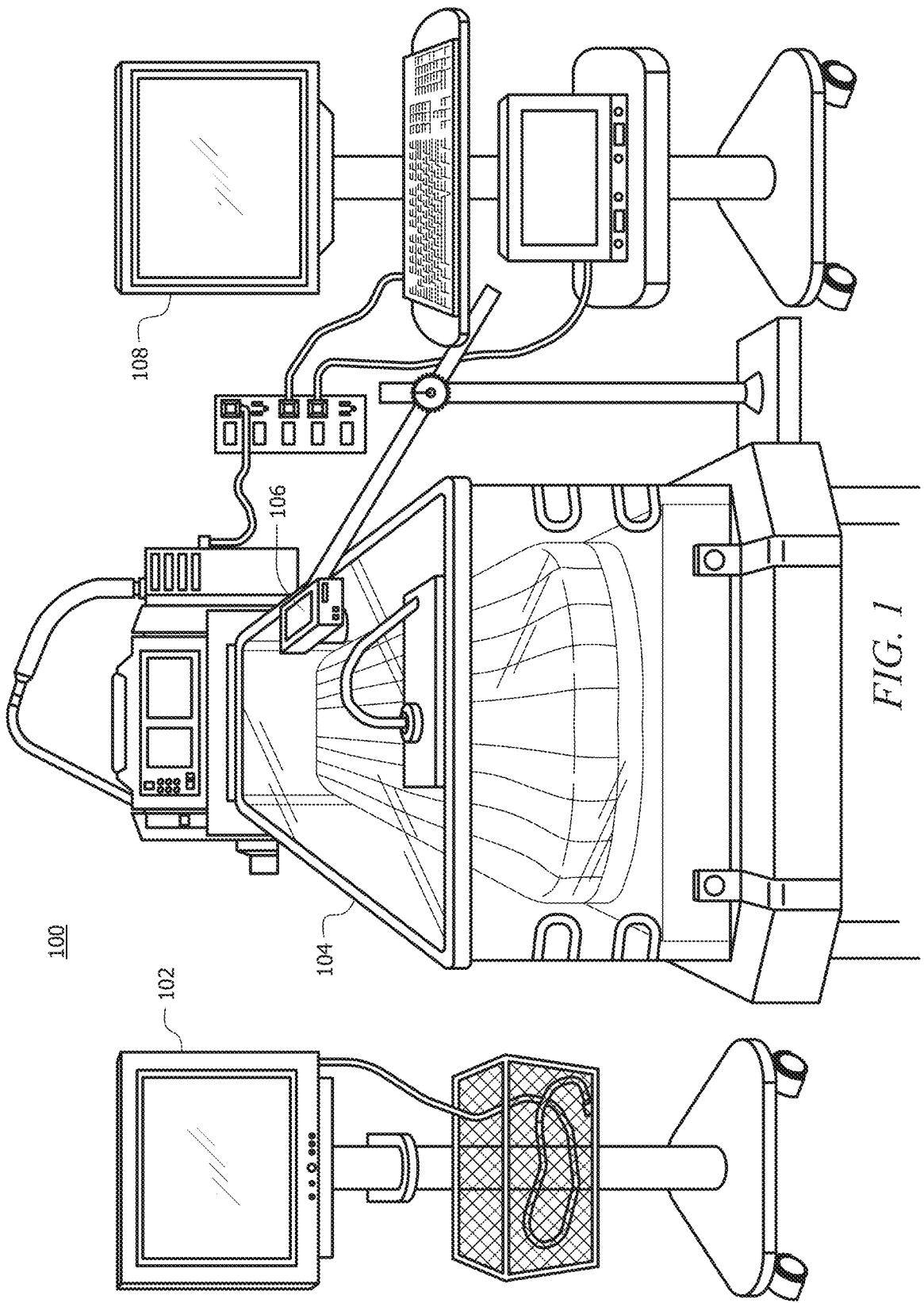
FIG. 1 is an image depicting the setup for data collection.

In the following detailed description, reference is made to the accompanying drawings, which form a part thereof, and within which are shown by way of illustration specific embodiments by which the invention may be practiced. It is to be understood that other embodiments may be utilized, and structural changes may be made without departing from the scope of the present application. These embodiments are described in sufficient detail to enable those of ordinary skill in the art to practice the present disclosure, and it is to be understood that other embodiments may be utilized, and that structural, logical, and electrical changes may be made within the scope of the disclosure.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. Only those process acts and structures necessary to understand the embodiments of the disclosure are described in detail below. A person of ordinary skill in the art will understand that some process components are inherently disclosed herein and that adding various conventional process components and acts would be in accord with the disclosure. In this description, specific implementations are shown and described only as examples and should not be construed as the only way to implement the present disclosure unless specified otherwise herein.

Illustrations presented herein are not meant to be actual views of any particular material, component, or system, but are merely idealized representations that are employed to describe embodiments of the disclosure. Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method but are merely idealized representations employed to more clearly and fully depict the present invention defined by the claims below.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Any headings used herein should not be considered to limit the scope of embodiments of the invention as defined by the claims below and their legal equivalents. Concepts described in any specific heading are generally applicable in other sections throughout the entire specification.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. In embodiments in the present application the human includes human infants. These infants include both term and preterm neonates as well as older infants.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a device. The proximal end of the device is defined as the end of the device closest to the user when the device is in use. The distal end is the end opposite the proximal end, along the longitudinal direction of the device, or the end furthest from the user.

The use of "including," "comprising," or "having," "containing," "involving," and variations thereof herein, is meant to encompass the items listed thereafter and equivalents thereof as well as any additional items a person of ordinary skill in the art would reasonably understand to be included.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method but are merely idealized representations employed to more clearly and fully depict the present invention defined by the claims below.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

In an aspect of the present disclosure, a system and method for monitoring intensity of pain experienced by one or more patients is provided. The one or more patients are pediatric patients, and more specifically these patients may be neonates. The method includes assessing the intensity of the pain experienced by each of the one or more patients on one or more pain monitoring scales by using one or more bio-markers, fetching the one or more bio-markers associated with each of the one or more patients by a plurality of bio-sensors, determining a correlation between the one or more bio-markers and the intensity of the pain experienced by each of the one or more patients and generating a pain profile of each of the one or more patients. The generated pain profile shows the intensity of pain experienced by each of the one or more patients at various points in body aiding in better medical treatment of each of the one or more patients.

In an embodiment of the present disclosure, the one or more pain monitoring scales include scales for measuring pain of one or more neonates, one or more infants or one or more toddlers. For example, the scales can be a neonatal pain agitation and sedation scale (N-PASS), a pain assessment tool (PAT), a bernese pain scale for one or more neonates (BPSN), Neonatal Infant Pain Scale (NIPS), wong-baker scale, a face, legs, activity, crying, and consolability (FLACC) scale, an expert physician's quantified pain scale and the like.

In another embodiment of the present disclosure, the one or more pain monitoring scales include a visual analog scale (VAS), a verbal numerical rating scale (VNRS), a brief pain inventory (BPI), verbal descriptor scale (VDS), the expert physician's quantified pain scale and the like. The one or more pain monitoring scales rank the intensity of the pain experienced by pediatric population who are mature enough to interpret perception of the pain on each of the one or more pain monitoring scales. Each of the pain monitoring scales rate the intensity of the pain, say from values 1 to 10. In an embodiment of the present disclosure, the value 10 can represent the highest pain level experienced by the pediatric population. Further, the method includes recording one or more bio-markers for each state in ranking of each scale.

In an embodiment of the present disclosure, the one or more bio-markers associated with each of the one or more users includes heart rate (HR), heart rate variability (HRV), skin conductance, respiration information, blood pressure, photoplethysmography (PPG), oxygen saturation, single or multiple lead electrocardiography (ECG), electroencephalography (EEG), muscle activity (EMG), pulse wave transit time, atrial kick, BCG (Balistocardiogram), EOG (Electrooculography), Dispersion based ECG, Impedence cardiography, GSR, $VO_2$ max, $PaCO_2$, cardiac output, oxygen saturation, blood glucose, blood gas, temperature, sweat, hydration, gaze.

In an embodiment of the present disclosure, the plurality of bio-sensors includes a finger-based pulse oximeter, an accelerometer, a respiration monitor and a 1-lead disposable electrocardiography (ECG) patch or a multiple lead ECG. In some embodiments the method of pain detection is augmented by the use of one or more of these bio-markers, or any combination of a plurality of these bio-markers.

In an embodiment of the present disclosure, the method distributes the one or more users into different sets based on their phenotypical characteristics, genotypical characteristics and mental attributes.

The intensity of pain experienced by the one or more patients is characterized by at least one of biological factors (gender, genetics and the like), psychological factors (mood, attention and the like), experimental factors, duration of measurement of the intensity of the pain and location of each sensor of the plurality of bio-sensors on the body of each of the one or more patients. The method can track the location of each of a plurality of bio-sensors on the body of the patient used to monitor a bio-marker.

In another aspect of the present disclosure, a system for monitoring intensity of pain experienced by one or more patients is provided. The one or more patients are pediatric patients. The system includes a plurality of bio-sensors to gather one or more bio-markers associated with each of the one or more patients and a pain monitoring application. These markers are tracked along with images gathered of the patients' faces in the pain monitoring application. The pain monitoring application further includes an input/output application to gather the one or more bio-markers associated with each of the one or more patients, a display application to display the one or more bio-markers associated with the one or more patients, a diagnostic application to assess the one or more bio-markers of each of the one or more patients to determine the intensity and location of the pain, a presentation application to generate a pain profile for each of the one or more patients and a database to store the gathered plurality of the one or more bio-markers associated with each of the one or more patients and the generated pain profile for each of the one or more patients. The generated pain profile shows the intensity of pain experienced by the one or more patients at various points in the body aiding in better treatment of the one or more patients.

In an embodiment of the present disclosure, the one or more pain monitoring scales include scales for measuring pain of one or more neonates, one or more infants or one or more toddlers. For example, scales can be a neonatal pain agitation and sedation scale (N-PASS), a pain assessment tool (PAT), a bernese pain scale for one or more neonates (BPSN), Neonatal Infant Pain Scale (NIPS), wong-baker scale, a face, legs, activity, crying, and consolability (FLACC) scale, an expert physician's quantified pain scale and the like. Each of the one or more pain monitoring scales rank the intensity of pain experienced by the one or more neonates, the one or more infants and the one or more toddlers.

In another aspect of the present disclosure, a contextual data gathering device is a computer system. The computer system includes one or more processors and a non-transitory memory containing instructions that, when executed by the one or more processors, causes the one or more processors to perform a set of automated steps. The set of steps includes assessing intensity of pain experienced by each of one or more patients on one or more pain monitoring scales by using one or more bio-markers, assessing intensity of pain using the images gathered of the patients, gathering the one or more bio-markers associated with each of the one or more patients by a plurality of bio-sensors, automatically combining the one or more bio-markers and physiological, and contextual data, to determine the intensity of pain experienced by each of the one or more patients and generating a pain profile of each of the one or more patients. The combination of bio-markers, and the images gathered to generate the pain profile is described in detail in the Example below. The generated pain profile shows the intensity of pain experienced by each of the one or more patients at various points in the body aiding in better medical treatment of each of the one or more patients.

In an embodiment, the medical device configured to collect physiologic data includes a finger-based pulse oximeter, an accelerometer, a respiration monitor and a 1-lead disposable electrocardiography (ECG) patch or a multiple lead ECG, an electroencephalography (EEG) sensor, or a muscle activity sensor.

In an embodiment the pain assessment system includes a medical device including a heart rate (HR) monitor, skin conductance monitor, respirator, blood pressure cuff, photoplethysmography (PPG) monitor, oxygen saturation monitor, single or multiple lead electrocardiography (ECG), electroencephalography (EEG), muscle activity (EMG) monitor, galvanic skin response (GSR) monitor, skin conductance monitor, pulse wave transit time monitor, atrial kick monitor, BCG (Balistocardiogram), EOG (Electrooculography), Dispersion based ECG, Impedence cardiograph, echocardiogram, blood sample equipment, thermometer, and urine catheter.

In an embodiment of the present disclosure, the non-transitory memory containing instructions that, when executed by the one or more processors, cause the one or more processors to perform a further step of combining the images gathered and the one or more bio-markers associated with each of the one or more patients and the intensity of the pain experienced by each of the one or more patients. In an alternative embodiment of the present disclosure, the computer system assesses the intensity of pain using only the images gathered of the patients.

These implementations are particularly advantageous in a number of respects. For instance, the implementations and combination of elements and techniques described herein are particularly beneficial as they allow rapid navigation and consumption of a significant quantity of information especially on a small sized display; reduce required computational resources; and reduce the data communication bandwidth required to retrieve the hierarchical data from a data server. The implementations are also advantageous because they provide a user interface that adapts to the amount of information that need to be presented, provides the data for easy hierarchy level traversal and allows high level scrubbing to transition easily between high level topics. For example, the techniques described herein allow a computing device to efficiently present an otherwise difficult to consume and navigate quantity of data from many categories and sources.

The techniques described herein are particularly beneficial as they allow rapid navigation and consumption of a significant quantity of information on a limited display (e.g., the screen on a computing device), reduce required computational resources (e.g., resulting in low latency), and reduce data communication bandwidth used. For example, the techniques described herein allow a computing device e.g., an inexpensive smartphone or wearable device (e.g., a smartwatch) with very limited computational resources and a very limited display size to efficiently present news from many categories and articles while using a limited quantity of data (e.g., many mobile device have slow data connections or limited cellular data plans allowing only a small amount of data to be downloaded).

Further, implementations of the system and method described herein are beneficial in improving the accuracy in the diagnosis and adequate treatment of pain, thereby improving resource allocation, and implementation of patient care. In some embodiments the system and method described allows graphical user interfaces to be specifically adjusted based on the data gathered from patients. For example, some computing devices have limited size displays that can display only a limited number of graphical elements. The system and methods described herein may automatically and dynamically format a graphical user interface to display only those graphical elements (or otherwise arrange or size the graphical elements) based on the data gathered from pateints.

In some implementations, the technology described herein differentiates between the signs and symptoms of pain experienced by a patient, in this case a pediatric patient, in order to further increase the accuracy of the image data and biomarker data estimation of experienced pain while reducing computational complexity, consumed bandwidth, quantity of data calls, and consumed computational resources. Compared with previous pain monitoring and diagnosing systems, the technology consumes fewer processing cycles to estimate and predict levels of experienced pain in pediatric patients, thereby allowing more efficient real-time update of the level of pain experienced by the patient being monitored.

A communication device is used in accordance with various embodiments of the present disclosure. The communication device executes a pain monitoring application. The pain monitoring application analyzes the intensity and area of the pain and model the pain to enable tailoring of the treatments accordingly. The pain monitoring application includes an input/output application, a display application, a diagnostic application, a presentation application and a database. The input/output application receives the one or more bio-markers and images from the plurality of bio-sensors and cameras associated with the patient. The display application displays the received plurality of the one or more bio-markers and images associated with the patient.

The diagnostic application assesses the intensity of the pain of the patient with the graphical images received from the camera and on one or more pain monitoring scales that include one or more scales for measuring the pain of the patient. The patient can be one or more neonates, one or more infants or one or more toddlers. The scales can be a neonatal pain agitation and sedation scale (N-PASS), a pain assessment tool (PAT), a bernese pain scale for one or more neonates (BPSN), Neonatal Infant Pain Scale (NIPS), wong-baker scale, a face, legs, activity, crying, and consolability (FLACC) scale, an expert physician's quantified pain scale and the like. Each of the one or more pain monitoring scales rank the intensity of pain experienced by the one or more neonates, the one or more infants and the one or more toddlers. This data is combined automatically with the images and sounds of the patients' face or body taken by the camera associated with the patient. This is described in detail in the Examples below.

The diagnostic application determines a correlation between the audio and video data collected with the patient's demographic data and in some instances the biomarker data gathered on the patient. The diagnostic application uses this correlation to provide an estimate of the intensity of the pain the patient is experiencing.

The diagnostic application is also capable of tracking the changes in video and audio data in real time with changes and locations of each of a plurality of biosensors gathering biomarker data on the patient. In another embodiment of the present disclosure, the diagnostic application tracks multiple measuring sites for the neonates in addition to the audio and visual data gathered on the patient. Further, the diagnostic application combines signal values including but not limited to images or sounds representing pain from the multiple sites of the body to create a composite signal as well as any of the plurality of biomarkers. Any disruption or deviation from baseline may be measured by comparing the composite signal from points/sites of the body that generates a clean signal.

The presentation application generates a pain profile of the patient which can show the intensity of the pain and the location of the pain in the patient. The automatically generated profile shows the intensity of the pain. The profile can also show the intensity at various locations on the body of the patient. The presentation application can use color to represent intensity of pain. In some embodiments a change in the intensity of the color codes is related to the pain experienced by the user. This color information and data is then displayed on the display application.

The output from the presentation application and the display application is stored in a database which stores the audio/visual and biomarker data from the patient. The database stores the pain profile and color representation of the pain profile of the patient in real time. The diagnostic application accesses the database to compare the audio/visual and biomarker data from the patient to stored values in the database. The diagnostic application provides automated comparison of the real time data to stored data to provide pain intensity measurements from the patient. In an embodiment of the present disclosure, if an image or audio file, or a bio-marker of the one or more bio-markers and/or the one or more pain monitoring scales indicates pain, the patient is reported to be experiencing the pain.

In an embodiment of the present disclosure, the one or more bio-markers associated with the patient includes the HR, heart rate variability (hereinafter 'HRV'), skin conductance, respiration information, blood pressure, photoplethysmography (hereinafter 'PPG'), oxygen saturation, electrocardiogram (hereinafter 'ECG') analysis, electroencephalogram (hereinafter 'EEG') analysis, muscle activity (hereinafter 'EMG'), restlessness and the like.

In another embodiment of the present disclosure, the one or more bio-markers associated with the patient including the HR, the BP, the respiratory information, the skin conductance and the like may be utilized to track the pain and the location of the pain in the body of the patient. Moreover, variability in the one or more bio-markers from the one or more bio-markers may serve as an indication of the intensity of the pain felt. For example, using an electrocardiography (ECG) with extremely high sampling rate enables modeling and analyzing of minute variations in the ECG morphology.

In yet another embodiment of the present disclosure, using respiration rate as the bio-marker, respiratory distress, frequency and depth can be monitored that indicates the patient's reactivity to the pain. Moreover, an increase in the respiration rate, an increase in shallow breathing and a loss of respiratory rhythm may indicate greater pain. Similarly, reduction in the HRV and elevation in the HR may indicate severity of the pain. The pain may be modeled and mapped by utilizing changes in low frequency (hereinafter 'LF') and/or high frequency (hereinafter 'HF') spectrum of the heart rate variability (HRV). For example, greater LF (reduced HF) indicates response to pain stimulus. Further, the skin conductance can be used to model and map the pain. For example, greater skin conductance measured by the galvanic skin response (GSR) serves as the bio-marker indicating the greater pain. Moreover, a noticeable and progressively increasing change in certain dimensions of the EEG reflects increasing pain.

Applications and Improvements

Certain embodiments of the claimed subject matter provide specific applications and ways of automating the creation of a pain profile of a patient incorporating elements form multiple sources in order to improve the diagnosis and treatment of pain in patients, specifically patients unable to communicate, such as neonates and babies.

Certain embodiments of the claimed subject matter provide improvements to the assessment, diagnosis, and treatment of pain in new borns. Certain embodiments of the claimed subject matter provide improvements to the storing physiological and contextual data gathered on patients, in some embodiments new borns, to improve long term pain diagnosis and treatment, as well as potential research opportunities dealing with pain diagnosis and treatment in neonates.

Certain embodiments provide a means for configuring memory to store the automated assessment, correlation, diagnosis, and patient profile creation using the methods described herein, providing a specific improvement in the memory storage and retrieval when creating patient profiles with regard to pain.

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C #, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

Example 1

Methods
A. Subject

Neonates (N=40, 50% female and 50% male) were recorded undergoing procedural (31 neonates) and postoperative (9 infants) pain. Heel lancing and immunization procedures are examples of the procedural pain stimuli and Gastrostomy Tube is an example of a postoperative pain stimulus. The age of the neonates ranges from 32 to 40 weeks of gestation (GW), with a mean age of 35.9 (2.8). Any neonate born in the range of 28 and 41 gestation weeks is eligible for enrollment after obtaining informed consent from the parents.

B. Pain Stimuli and Ground Truth Labeling

Data were collected during procedural and postoperative pain by bedside caregivers in the presence of a research assistant and the principal investigator. The painful procedures that trigger procedural pain are routine heel lancing and immunization. The recording for procedural pain consists of eight time periods: baseline period (T0), procedure preparation period (T1), the painful procedure period (T2), and five post-painful-procedure periods (T3 to T7).

The pain score for each of these periods was documented by bedside caregivers using the Neonatal Infant Pain Scale (NIPS). This pain scale consists of facial expression, cry, arms and legs movement, vital signs, and state of arousal. The label for each pain response is 0 or 1 except for crying, which can be labeled as 0, 1, or 2. Adding the labels of NIPS's components generates a total pain score, which is used to generate, through thresholding, three emotional states or labels: no pain, moderate pain, and severe pain. These states provide the ground truth labels that are used to train the machine learning classifiers.

As for postoperative pain, neonates were recorded for 15 minutes prior a major surgery (e.g., Gastrostomy tube and Omphalocele repair) to get their baseline state and for three hours after the surgery. The pain score was documented by bedside caregivers, during the baseline and every 15 minutes during the postoperative state, using Neonatal Pain, Agitation and Sedation Scale (N-PASS). This pain scale consists of facial expression, crying irritability, behavior state, extremities tone, and vital signs. The label for each pain response ranges from −2 to 2. Adding the labels of N-PASS components generates a total pain score that ranges from −10 to 10. Performing a thresholding on the generated score provides four emotional states, which are deep sedation (−10 to −5 score), light sedation (−5 to −2 score), normal (less than −2 score), and pain (larger than 3 score). These states provide the ground truth labels that are used to train the machine learning classifiers.

Caregivers who documented the NIPS and NPASS scores underwent a standardized training program to ensure proper utilization of the tools. Each epoch was scored independently by two trained caregivers so that interrater reliability can be established using coefficient kappa to measure the inter-observer agreement. We include all the cases of agreement and exclude the cases of disagreement (below 5%) from further analysis.

C. Collected Data

The collected data is presented below, the equipment utilized to collect them, and the synchronization procedure. The setup of data collection is depicted in FIG. 1.

The system 100 depicted in FIG. 1 includes a physiological data monitoring device 102; a contextual data monitoring device 108; an incubator 104 (for neonates) which can alternatively be a crib, or any bed; and an audio/video data gathering device 106. The patient not depicted would be in the incubator 104 and attached to the physiological data monitoring device 102 via a plurality of bio-sensors (not depicted). The audio/video data gathering device 106 would be place above the patient's incubator 104 in a manner to allow for the capture of sounds from the patient as well as facial expressions and body movements.

1) In some embodiments the audio/video data gathering device 106 is a video camera which can be used to record video and audio signals. The camera is triggered remotely using an application installed on a smartphone or alternatively on the contextual data monitoring device 108. The recorded data includes the infant's face, head, and body as well as the sounds of neonates and background noise (e.g., sounds of equipment and nurses).

2) The physiological data gathering device 106 is configured to ensure data synchronization, caregivers manually mark the start and end points of data collection by simultaneously inserting a timestamped-event to the physicolical data gathering device 106 and, in some embodiments, using clapperboard with the video/audio stream. A caregiver can also mark, using the same method, the time of assessing pain by the bedside caregivers.

3) The contextual data monitoring device 108 collects several contextual data. These data can include the Gestational Age (GA), clinical data (e.g., the medication type/dose), birth-weight, race/ethnicity, gender, and non-pharmacological interventions (e.g., oral sucrose and the pacifier use). The contextual data monitoring device 108 collects all the data collected during routine clinical procedures and carried out in the normal clinical environment that is only modified by the addition of the cameras. This makes the database more challenging and representative of the real-world condition.

D. Preprocessing and Tracking

The preprocessing operations (e.g., face and body tracking) performed on video, audio, and vital signs are presented below.

1) Video: The first step of preprocessing involves dividing the recorded time periods (described in Section III.B) into segments of five, ten, and fifteen seconds. Then, a standard histogram equalization was performed on low-light videos to enhance their contrast. Next, the neonate's face and body were tracked in each frame as described next.

Figure 2B:
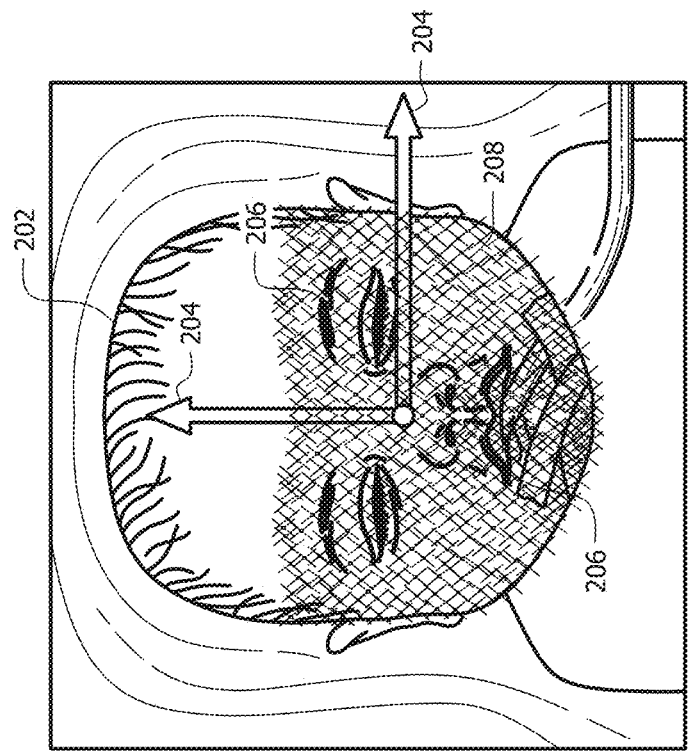
FIG. 2B depicts the patient with Zface 49 points, the mesh points, and the head orientations of the patient.
Figure 2A:
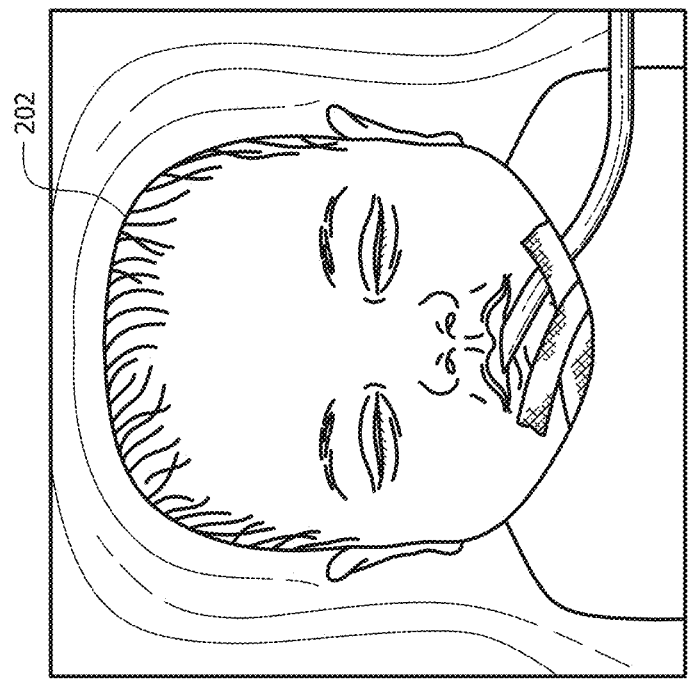
FIG. 2A depicts a patient according to an embodiment of the invention.

For face tracking, ZFace is applied [24], or any equivalent tracker, which is a person independent tracker, in each video to obtain 49 facial landmark points and face's boundary points. The tracker outputs the coordinates of a mesh of points, 6 degrees of freedom of rigid head movement, and a failure message to indicate the failure frames. The percentages of the missing frames for example, for no pain videos in the database is approximately 8%. After obtaining the required points in each frame, we used them for image registration and facial region cropping. FIG. 2A depicts the patient 202 as the patient appears on the video camera. FIG. 2B shows the 49 points depicted as bold lines 206 in FIG. 2B as well as the mesh 208 which includes 512 points. FIG. 2B also depicts the arrows 204 indicate angles estimation.

Figure 3:
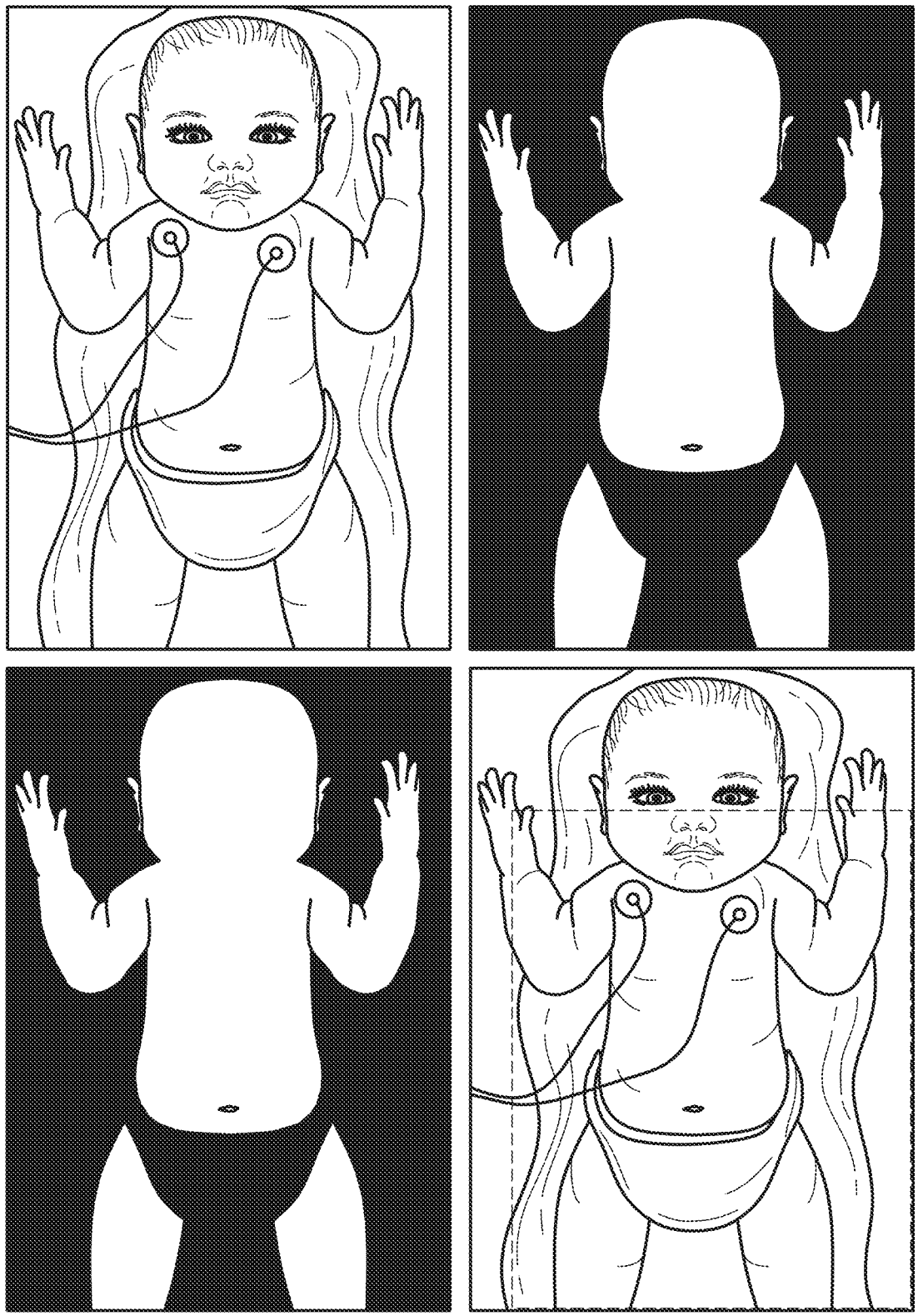
FIG. 3 is a series of images depicting (first row) the original binary image before morphological operations and (second row) the binary image after morphological operations, detected by ROI.

For body region tracking, a classical color-based tracking method is implemented to detect the body region in each frame. The first step of the method involves creating a total of 6052 patches, half of which were body patches and the other half were non-body patches, with size 128×128. After creating the patches, they are converted to YCbCr (Luminance; Chroma: Blue; Chroma: Red) color space and generated the Cb and Cr histograms of these patches. Next, the normal distribution of these histograms is generated. The normal distributions of CB channel for body and no-body patches showed a relatively high degree of overlapping while the normal distributions of CR channel were relatively separated. Then, the cut-off point (i.e., the cross point of body and non-body normal distributions) of CR histogram is detected that gives the smallest error. The detected cut-off point was used as a threshold to convert the frame into binary images, which was pruned using morphological operations. Finally, the nose-tip point was used and considered the region below this point as the region of interest (ROI). This method fails in cases when the neonate's body is occluded, or it is covered with a blanket that has a similar color to the background. In these cases, the location of the body in the first frame is manually detected and tracked it over all frames. FIG. 3 shows the algorithm's result in detecting the body region of a neonate and the black and white silhouette created by the system to monitor, for example, body movements.

2) Audio: The segmented audio signal was divided into several Hamming windows of 32-millisecond that shifts every 16-millisecond and Hamming windows of 30-millisecond that shifts every 10-millisecond to minimize the signal discontinuities. The first windowing scheme is used with the Linear Predictive Cepstral Coefficients (LPCC) and the second is used with the Mel Frequency Cepstral Coefficients (MFCC). No filtering or background noise removal operations were performed prior to feature extraction.

3) Vital Signs: To remove the outliers from the extracted physiological data including vital signs (i.e., HR, RR, and SpO2) numbers, median filter is applied with different window sizes. Then, several descriptive statistics are calculated (e.g., mean, standard deviation, max) for vital signs readings across the pain or no pain event (i.e., 3× statistics dimensional vector for each event).

Feature Extraction and Fusion

In this section, the feature extraction methods are presented for facial expression, body movement, and crying sound as well as the fusion methods that combine these data with the physiologic data including vital signs features.

A. Facial Expression

Two feature extraction methods, namely strain-based and geometric-based, were implemented to extract pain-relevant features from neonates' face. These methods are presented below.

1) Strain Features: The strain features were extracted using an algorithm which was described thoroughly in [46]. As discussed in [46] the strain-based method used to detect facial expressions of infants consists of two stages: face tracking and expression segmentation. In the face tracking stage, the infant's face in each video frame is detected using a Viola-Jones face detection method. The infant's face classifier is built using a cascade of boosted Haar-like classifiers trained with images of infants' face under different poses and occlusions. The classifier is able to successfully detect faces with frontal/near-frontal views. Faces with severe poses/strong occlusions were missed and thus are excluded from further analysis. After the face images were obtained, facial landmark points are applied using an algorithm to extract 68 points. These points are used then to align the face, crop it, and divide it into four regions. The problem can be formulated as:

$$\underset{W^r, \{W^a\} a \in A}{\mathrm{argmin}} \sum_{i=1}^{N} l^r(y_i^r, f(x_i; W^r)) + \sum_{i=1}^{N} \sum_{a \in A} \lambda^a l^a(y_i^a, f(x_i; W^a))$$

Where $f(x_i; w^r)$ is a function of $x_i$ and parameterized by a weight vector wr. The loss function is denoted by l(−). A typical choice is the least square for regression and the hinge loss for classification. The main task "r" in facial landmark detection is optimized with the assistances of a number of related and auxillary tasks a∈A. The $\lambda^a$ denotes the importance coefficient of a-th task's error and the regularization terms are omitted for simplification. The algorithm combines regression and classification, and focuses on a shared input representation $x_i$. Therefore, the objective function can be rewritten as:

$$\underset{W^r, \{W^a\}}{\mathrm{argmin}}$$
$$\frac{1}{2} \sum_{i=1}^{N} \|y_i^r - f(x_i; W^r)\|^2 - \sum_{i=1}^{N} \sum_{a \in A} \lambda^a y_i^a \log(p(y_i^a | x_i; W^a)) + \sum_{t=1}^{T} \|W\|_2^2$$

The use of this algorithm to formulate a landmark detection model is discussed in Z. Zhang, et al., *Facial Landmark Detection by Deep Multi-task Learning*, European Conference on Computer Vision, Springer, 2014, pp. 94-108, which incorporated herein by this reference.

This algorithm consists of five main steps. First, the face region detected as discussed in Section III.D is divided into four regions (I, II, III, and IV). The optical flow is calculated between consecutive frames of a video for each region of the face as well as the overall face region. Then, the optical strain is estimated over the flow fields to generate the strain components of the strain tensor. After generating the strain components, the strain magnitude (εM) is calculated for each region of the face along with the overall face region and normalized; each region generates a sequence corresponding to the amount of strain observed over time. Lastly, a peak detector method is applied to the strain plots obtained for each region from I to IV to detect the points of maximum strain, which correspond to facial expressions. To form the feature vector for classification, computed several descriptive statistics are computed (e.g., mean, standard deviation, and 25th percentile) for the detected maximum strain values and concatenated them into 5 facial regions×S dimensional vector, where S represents the number of statistics.

2) *Geometric Features:* The Neonatal Facial Coding System (NFCS) is an extension of Facial Action Coding System (FACS) designed specifically for neonatal pain. Examples of NFCS pain-relevant facial movements include eye squeeze, bulging brow, deepening of the nasolabial furrow, horizontal mouth stretch, vertical mouth stretch, and pursed lips. Using the points detected by ZFace (see Section III.D), eleven Euclidean distances between landmark points to represent the above-mentioned NFCS facial movements are computed:

Eye squeeze: defined as a reduction of the distances between the upper and lower eyelids of left eye (d1) and right eye (d2) or reduction of distances between the highest arch's points and upper eyelids of left eye (d3) and right eye (d4).

Bulging brow: defined as reduction of the distance between inner corners of eyebrows (d5) or a reduction of the distance between the highest arch's points of left and right eyebrows (d6).

Deepening of the nasolabial furrow: defined as the increase in the distance between the nose's left end point and the mouth's left corner point (d7) or the increase in the distance between the nose's right end point and the mouth's right corner point (d8).

Vertical mouth stretch: defined as the increase in the distance between the mouth's upper and lower points (d9).

Horizontal mouth stretch: defined as the increase in the distance between the mouth's left and right corner points (d10).

Jaw drops: defined as the increase in the distance between the nose's tip and the lowest point of the lower face boundary or chin's tip (d11).

To form a feature vector for classification, several statistics (e.g., mean, standard deviation, 75th percentile) for each distance were calculated across frames and concatenated into 11×S dimensional vector, where S represents the number of statistics.

B. Body Movement

Body movement analysis depends on the motion image, which is a simple and efficient method to estimate an infant's body movement in video sequences [46]. It identifies the change of each pixel value between consecutive frames. Each pixel in the motion image M (x; y) has a value of 0 to represent no movement or 1 to represent movement. To analyze the infant's body movement, we computed the motion images between consecutive video frames. Then, we applied filtering to reduce noise and get the maximum visible movement. In assessing infants' pain, care providers focus on observing the amount of body movement along with the speed and pattern. Hence, we used the amount of body motions in each video frame as the main feature for analyzing infants' body movement. This feature is computed as follows:

$$A_m = \frac{1}{N_x N_y} \sum_{x=1}^{N_x} \sum_{y=1}^{N_y} M(x, y) \quad (1)$$

Where Nx and Ny represent the image's height and width. To find the total amount of motion in each video sequence, we summed Am as:

$$Total_{motion} = \sum_{k=1}^{F} A_m^k \quad (2)$$

Where F is the total number of frames. For classification, thresholding is applied on Total(motion) to classify body movement as pain related (score 1) or not pain related movement (score 0). The generated Total(motion) value is the main feature that is used for classification.

C. Crying Sound

To analyze neonatal cry, we applied two Cepstral Domain methods: Linear Predictive Cepstral Coefficients (LPCC) and Mel Frequency Cepstral Coefficients (MFCC). LPCC (20 coefficients) were computed from 32-millisecond window with 16-millisecond offset while MFCC (20 coefficients) were computed from 30-millisecond window with 10-millisecond offset. The lengths of LPCC and MFCC feature vectors are L×320-dimensions and L×200-dimensions respectively, where L represent the length of audio instance. The extracted feature vectors were then reduced using vector quantization method as follows:

The extracted features or coefficients of all audio instances using k-mean algorithm were clustered.

The centroid (a.k.a. codeword) for each cluster or group were computed.

A codebook matrix was generated from the groups' centroids, the rows of this matrix represent the group ID and the columns represent the centroids. The generated codebook has a total of 32 groups.

The stored codebook is used to map a new instance to the group whose center is close to this instance features.

D. Fusion

In this section, the feature-level and decision-level methods for combining different pain responses to generate a multimodal pain assessment is described. As presented below, the fusion methods combine facial expression, crying, body movement, and and physiologic data (such as vital signs). This is the first work that assesses neonatal pain using a combination of these pain responses.

1) *Feature-level Fusion:* Feature-level fusion is the process of combining multiple modalities (i.e., pain responses) in the early stage by concatenating the features of these responses into a single high-dimensional feature vector. The concatenated vector is then used for classification. Feature-level fusion has three main issues: scaling, the high-dimensionality of the feature vector, and the missing data or feature.

The extracted features of each pain modality or response were normalized in the range [0,1] for scaling before concatenating them into a single feature vector. For feature reduction, two feature selectors, namely Relief-f and Symmetric Uncertainty, were applied. To handle the missing feature issue, we trained a classifier for each case of missing feature. For example, given that S=x1; x2; x3; ..., xf, where x represents a feature, f represents the total number of features, and x1 feature is missing, the classifier is trained using all the features except x1. The total number (N) of the trained classifiers is computed as:

$$N = \sum_{i=1}^{f-1} {}^f C_i$$

f-1 indicates the ease when all the features are missing (i.e., $^fC_i$ where f=i).

2) Decision-level Fusion: The decision-level fusion represents a variety of methods designed to merge the decisions or outcomes of multiple classifiers into one single ensemble decision. To combine the outcomes of different pain responses, a simple majority voting scheme is applied as described in [47]. In the majority-voting scheme, each pain response contributes one vote (i.e., class label) and the majority label in the combination is chosen as the final decision or outcome. If the combination of different pain responses has a tie, the class that has the highest confidence score as the final outcome is chosen.

Classification and Model Evaluation

After extracting the features of each pain response, these features are used to train different machine learning classifiers. Particularly, Naive Bayes, Nearest Neighbors (kNN), Support Vector Machines (SVMs), and Random Forests (RF) classifiers since are trained because they have shown good classification performance in pain assessment applications [44], [32].

The classifiers were built in case of feature-level fusion as explained previously. In case of decision level fusion, a single classifier is built for each pain response and then combined using the majority voting scheme.

To evaluate the trained classifier and estimate the generalization performance, two evaluation protocols are used: subject level 10-fold cross validation and leave-one-subject-out cross validation. The 10-fold cross validation is used to evaluate the performance of the general model and leave one-subject-out cross validation to evaluate the performance of the specific models.

Experimental Results and Discussion

In this section, the results are reported of assessing neonatal procedural pain of all the 31 neonates as well as the results of assessing pain for a specific group of neonates such as the female group. These results are then compared with the results of existing similar works.

TABLE 1

Unimodal and multimodal pain assessment for general model

|  | $F_S$ | $F_G$ | B | C | VS | FF | DF |
|---|---|---|---|---|---|---|---|
| Accuracy | 84 | 88 | 85 | 82 | 81 | 90 | 94 |
| AUC | 0.72 | 0.82 | 0.77 | 0.69 | 0.72 | 0.87 | 0.83 |

A. General Model

To assess neonatal procedural pain, two sets of experiments were conducted. In the first experiment, a single pain response was used to classify the emotional state of 31 neonates into pain or no-pain (unimodel). In the second experiment, different pain responses were combined, using feature-fusion and decision-fusion, to classify the emotional state of 31 neonates into pain or no-pain (multimodal). The 10-fold cross validation was used for evaluation as follows:

The 31 subjects were divided into 10 folds (i.e., each fold has approximately 3 subjects).

The classifier is trained using 9 folds and tested on the 10th fold.

The process was repeated (step 2) 10 times and calculated the average accuracy by averaging the accuracies of testing the classifier on the testing folds.

Table 1 presents the results of the first experiment ($2^{nd}$ to 6th columns) and second experiment (columns 7th and 8th). FS, FG, B, C, VS, FF, and DF are abbreviations for facial strain, facial geometric, body movement, crying, vital signs, feature fusion, and decision fusion, respectively. As can be seen in the table, the results are reported using the average accuracy and the Area Under the Receiver Operating Characteristic Curve (AUC).

The best assessment result (88% accuracy and 0.82 AUC) of the unimodal was obtained using the geometric features of facial expression. The strain features of facial expression achieved 84% accuracy and 0.75 AUC. However, the difference of AUC between the geometric features and strain features is not significant (p<0.05). The strain features achieved lower performance because the strain, derived from the optical flow, is not stable and is sensitive to other motions (e.g., sucking on a pacifier). The geometric features, which were computed according to the NFCS, are considered more pain specific features.

The body movement has the second-best performance (85% accuracy and 0.77 AUC) for the unimodal experiment; however, the AUC difference between body movement and facial geometry is not significant (p<0.05). Crying achieved 82% accuracy and 0.69 AUC. Cleaning the sound signals and removing background noise would improve the cry's performance in assessing pain. Finally, vital signs achieved the lowest assessment performance (81% accuracy and 0.72 AUC).

As for the multimodal experiment, the decision fusion achieved better accuracy (94%) than the feature fusion (90%). However, the AUC of the decision fusion (0.83) is lower than the AUC of the feature fusion (0.87). This means that the feature fusion performance of the pain class is better than the decision fusion. Although the AUC of the feature fusion is higher than the decision fusion, the difference of AUC between them is not significant (p<0.05).

To summarize, the best assessment accuracy of the unimodal experiment was obtained using the geometry of facial expression and the lowest was obtained using the vital signs. These results are consistent with previous findings [22] that facial expression is the most common and specific response of pain and that vital signs are less pain specific since they can be associated with other conditions such as noise, hunger, age, or underlying disease. Combining multiple pain modalities achieved better accuracy (decision: 94%, feature: 90%) than using a single pain response. The multimodal approach for pain assessment is mandatory because it allows to assess pain during circumstances when not all pain responses are available secondary to occlusion (e.g., stomach-down sleep and swaddling), clinical condition (e.g., Bell's palsy), level of activity (e.g., physical exertion), and sedation.

B. Specific Model

The following describes the result of assessing pain for a specific group of neonates. The neonates were divided into groups according to their gender (female and male), gestational age (preterm and full term), birth-weight (low weight and normal weight), and race (Hispanic and Non-Hispanic), built a model for each group, and reported each model's performance using the average accuracy and the AUC. The average accuracy was obtained by averaging the accuracies of subjects (i.e., leave-one-subject-out cross validation); Table 2 shows the number of subjects in each group.

TABLE 2

Demographic data of neonates

|  |  | Procedural | Postoperative |
|---|---|---|---|
| Gender | Female | 15 | 5 |
|  | Male | 16 | 4 |

TABLE 2-continued

Demographic data of neonates

| | | Procedural | Postoperative |
|---|---|---|---|
| Age | Preterm (<37 GW) | 14 | 4 |
| | Full term (37 to 42 GW | 17 | 5 |
| Ethnicity | Hispanic | 9 | 5 |
| | Non-Hispanic | 22 | 4 |
| Birthweight | Low (<2,500 gm) | 10 | 4 |
| | Normal (>=2,500 gm) | 21 | 5 |
| Total for procedural and postoperative | | 31 | 9 |

Table 3 presents the unimodal and multimodal pain assessment for female and male neonates ($2^{nd}$ column), preterm and full-term neonates (3rd column), low birth weight and normal-birthweight neonates (4th column), and Hispanic and Non-Hispanic neonates (5th column).

TABLE 3

Unimodal and multimodal pain assessment for specific models

| | | Gender | | Age | | Weigh | | Race | |
|---|---|---|---|---|---|---|---|---|---|
| | | | | | Full | | | | Non- |
| | | Female | Male | Preterm | term | Low | Normal | Hispanic | Hispanic |
| Facial | Accuracy | 70 | 76 | 76 | 72 | 74 | 73 | 76 | 77 |
| strain | AUC | 0.76 | 0.82 | 0.76 | 0.78 | 0.73 | 0.79 | 0.80 | 0.71 |
| Facial | Accuracy | 82 | 85 | 87 | 85 | 81 | 81 | 81 | 80 |
| Geometric | AUC | 0.78 | 0.80 | 80.80 | 0.83 | 0.78 | 0.81 | 0.76 | 0.79 |
| Body | Accuracy | 78 | 78 | 83 | 73 | 84 | 77 | 81 | 78 |
| Movement | AUC | 0.76 | 0.74 | 0.81 | 0.73 | 0.75 | 0.72 | 0.78 | 0.67 |
| Crying | Accuracy | 75 | 74 | 68 | 70 | 72 | 74 | 65 | 72 |
| Sound | AUC | 0.67 | 0.74 | 0.68 | 0.72 | 0.65 | 0.76 | 0.76 | 0.69 |
| Vital | Accuracy | 80 | 78 | 80 | 70 | 76 | 74 | 77 | 79 |
| Signs | AUC | 0.79 | 0.68 | 0.77 | 0.68 | 0.67 | 0.66 | 0.79 | 0.73 |
| Feature | Accuracy | 85 | 80 | 84 | 74 | 76 | 78 | 76 | 85 |
| Fusion | AUC | 0.79 | 0.73 | 0.76 | 0.73 | 0.71 | 0.69 | 0.73 | 0.84 |
| Decision | Accuracy | 92 | 89 | 94 | 89 | 94 | 89 | 88 | 92 |
| Fusion | AUC | 0.75 | 0.81 | 0.87 | 0.85 | 0.88 | 0.86 | 0.81 | 0.83 |

1) Gender Models: The male model has a higher pain assessment accuracy than female model for both the facial strain and geometric features (i.e., approximately 6% higher for strain and 3% higher for geometric). However, the AUC difference between the male model and the female model is not significant (p<0.05). These results suggest that there might be an association between pain expression and gender.

In case of body movement, the male model has the same accuracy as the female model, and the AUC values of both models are very similar. Likewise, the pain assessment accuracy of crying for the male model is very similar to the female model, and the difference of AUC between female and male is not significant (p<0.05). As for the vital signs, the accuracy of the male model is approximately 2% higher than the female model, but the difference of AUC between female and male is not significant (p<0.05).

The feature fusion's performance of the female model (85% accuracy and 0.79 AUC) is higher than the male model (80% accuracy and 0.73 AUC). Similarly, the accuracy of the female model in the case of decision fusion is higher than the male model; however, the AUC value of the male model is higher than the female model. Although the performance of pain assessment differs between the female and male models, the difference of AUC between them is not significant (p<0.05) for both feature fusion and decision fusion.

2) Gestational Age Models: The preterm model has a higher pain assessment accuracy than the full-term model for both facial strain and geometric features (i.e., approximately 4% higher for strain and 2% higher for geometric). However, the AUC difference between the preterm model and the fullterm model is not significant (p<0.05). The lower accuracy of full-term model might be attributed to the wider range of expressions this group has, as compared to the preterm group whose dominant expression is the pain expression.

In the case of body movement, the preterm model has a higher pain assessment accuracy than the full-term model (preterm: 83%, full term: 73%). The AUC for the preterm model is also higher; however, the difference of AUC between the two models is not significant (p<0.05). This result might be attributed to the high frequency of body movement of the older neonates in our dataset as compared to the preterm neonates. This result suggests that there might be an association between the neonates' movement and their gestational age.

As for crying, the difference of the accuracy of pain assessment between the preterm and full-term models is approximately 2%, and the difference of AUC between them is not significant (p<0.05). The accuracy of assessing pain based on vital signs for preterm neonates is relatively higher than full-term neonates. However, the difference of AUC between the two models is not significant (p<0.05). The inter-individual differences might be the reason behind the difference in the accuracy of vital signs between the preterm and full-term groups.

The feature fusion's performance of the preterm model (84% accuracy and 0.76 AUC) is higher than the full-term model (74% accuracy and 0.73 AUC). Similarly, the accuracy of the preterm model in the case of decision fusion is higher than the full-term model. Although the accuracy of pain assessment differs between the preterm and full-term models, the difference of AUC between them is not significant (p<0.05) for both feature fusion and decision fusion. Previous pediatric studies [38] reported a strong association between neonates' age and their response to painful stimulus.

The results presented above, specifically the accuracy of fusion, suggest that the gestational age of neonates might have an impact on their pain response.

3) Birthweight Models: The accuracy of pain assessment for low and normal weight are similar using facial strain and facial geometric, and the difference of AUC between low and normal models is not significant (p<0.05). Also, the accuracy of pain assessment for low and normal weight using crying analysis and vital signs changes are similar, and the difference of AUC between them is not significant (p<0.05). As for the body movement, the normal birthweight neonates have lower accuracy than the low birthweight neonates. It is worth mentioning that many of the neonates in the low-birthweight group are preterm neonates.

The feature fusion's performance of the low-birthweight model is similar to the normal-birthweight model. On the other hand, the decision fusion's performance of the low-birthweight model is higher than the normal-birthweight model. The difference of AUC between the low and normal models is not significant (p<0.05) for both feature fusion and decision fusion.

The results presented above suggest that there is no association between neonates' birthweight and their response to pain. The reduction of accuracy in some cases (e.g., body movement) is attributed to the age not the birthweight.

4) Race Model: The performance of pain assessment for Hispanic group is similar to Non-Hispanic group in the case of facial strain and geometry. The accuracy of pain assessment of the Hispanic model is higher than Non-Hispanic model for body movement, but lower for crying sound. However, the difference of AUC between Hispanic and Non-Hispanic models is not significant (p<0.05) for both body movement and crying. As for the vital signs, the difference of accuracy between the Hispanic and Non-Hispanic models is around 2%, and the difference of AUC is not significant (p<0.05). The pain assessment performance of both the feature fusion and decision fusion is lower for the Hispanic group, but the difference of AUC between the Hispanic and Non-Hispanic groups is not significant (p<0.05) for both feature fusion and decision fusion. The lower accuracy of the Hispanic group can be attributed to the small number of subjects in this group (see Table 2).

C. Comparison to the State of the Art

There are two ways to compare this novel system and method with the state of the arts in neonatal pain assessment. The first way is to apply this pain assessment approach to existing publicly available neonatal databases and report the results. This way is not possible since the only publicly available dataset (COPE) consists of static images of a single pain response (i.e., facial expression). The second way is to re-implement the state-of-the-art methods and apply them to this dataset. We have re-implemented Fotiadou et al. [17] method and applied it to this dataset. However, the obtained performance of this re-implementation was quite different than the performance reported in [17]. The choice of specific parameters and thresholds, due to the limited technical details provided in [17], affected the re-implementation and therefore led to a quite different result.

Thus, the performance of this novel system and method was compared with the performance of other methods as reported in the art. Particularly, this novel system and method of assessing pain expression was compared with [17] and the results described in this application for assessing pain using cry with [39]. As previously mentioned, this novel system and method is the first to assess neonatal pain based on body movement analysis and a combination of face, sound, and body in correlation with physiologic and contextual data. Therefore, we have not provided any comparison for pain assessment using body movement or multimodal methods. Fotiadou et al. [17] reported 0.98 AUC value in detecting pain expression of eight neonates (15 videos). This performance was obtained by varying the decision thresholds of the SVM classifier, which was evaluated using leave-one-subject out cross-validation. The algorithm in this disclosure achieved 0.82 AUC value in detecting the pain expression of 31 neonates (>200 videos). These results were obtained by varying the decision thresholds of the SVM classifier, which was evaluated using a subject level 10-fold cross validation.

Vempada et al. [39] reported 80.56% average accuracy in detecting the pain cry from 120 cry corpus. This performance was obtained using SVM classifier, which was evaluated on a testing set. The algorithm used in this disclosure achieved 82.35% average accuracy in detecting pain cry of 31 neonates (>200 corpus). This accuracy was obtained using SVM classifier, which was evaluated using a subject level 10-fold cross validation. These results are encouraging and show that the performance of the proposed algorithms is comparable to the state of the art of automatic pain assessment.

Conclusion

Infants receiving care in the NICU experience several painful procedures during their hospitalization. Assessing neonatal pain is difficult because the pain responses are nonspecific and vary by developmental stage or gestational age. The existing tools used for the assessment of neonatal pain are subjective and fail to meet rigorous psychometric standards. In addition, they do not provide continuous monitoring. Because aberrant central nervous system development and subsequent long-term impairment can result from both the failure to recognize and treat pain as well as the use of pharmacologic treatments in the absence of pain, developing continuous and consistent systems for the assessment of neonatal pain is important and may lead to improve outcomes of neonatal care.

Example 2: Prophetic

In some embodiments, the claimed subject matter would include the postoperative pain along with the procedural pain. The embodiments would improve the pain assessment performance of crying by employing or implementing a method that separates the neonate's sound from the environmental noise (e.g., sounds of nurses, parents, other infants around, and equipment).

Further collection of data of neonates during procedural and postoperative painful procedures would be used to investigate the use of deep features along with the hand-crafted features for pain assessment. Specifically, an investigation of the association between neonatal pain and the brain's hemodynamic activities using Near-infrared Spectroscopy (NIRS) would be completed. NIRS readings would provide a more objective measure of pain and can be used as a verification indicator.

The automatic system would generate continuous and standardized pain scores comparable to those obtained by conventional nurse-derived pain scores. The system would achieve 90% and 94% accuracies using feature fusion and decision fusion of different pain responses that are recorded in a challenging clinical environment. Because several pediatric studies reported the impact of contextual or medical information (e.g., gestational age) on pain, group-specific models would be built, namely female and male models, preterm and full-term models, low birthweight and normal birthweight models, and Hispanic and Non-Hispanic models, and their performance would be compared.

Example 3

FIG. 4 illustrates an embodiment of the system 400 showing a block diagram of the communication device 402. The communication device 402 executes a pain monitoring application 404. The pain monitoring application 404 analyzes the intensity and are of the pain. The pain monitoring application 404 includes an input/output application 406, a display application 408, a diagnostic application 410, a presentation application 412, and a database 414. The input/output application 406 receives the one or more biomarkers from a plurality of bio-sensors and audio/visual data from the patient. The display application 408 displays the data from the input/output application 406.

The diagnostic application 410 assess the intensity of pain of the patient using one or more pain monitoring scales that include one or more scales for measuring the pain of the user as well as the data from the input/output application 406. The presentation application 412 generates a pain profile of the patient. The generated pain profile shows the intensity of the pain at various points in the body of the patient to improve the diagnosis of pain and medical treatment of the patient. The pain profile can be generated using color codes with respect to location and intensity of the pain experienced by the patient. A change in intensity of the colors is directly proportional to the pain experienced by the patient. Moreover, the display application 408 displays the generated pain profile of each of the patients.

The database 414 stores the gathered data from the input/output application 406 and the generated pain profile from the presentation application 412. In some embodiments the diagnostic application 410 compares experimental results stored in the database 414 with the data from the input/output application 406.

Figure 5:
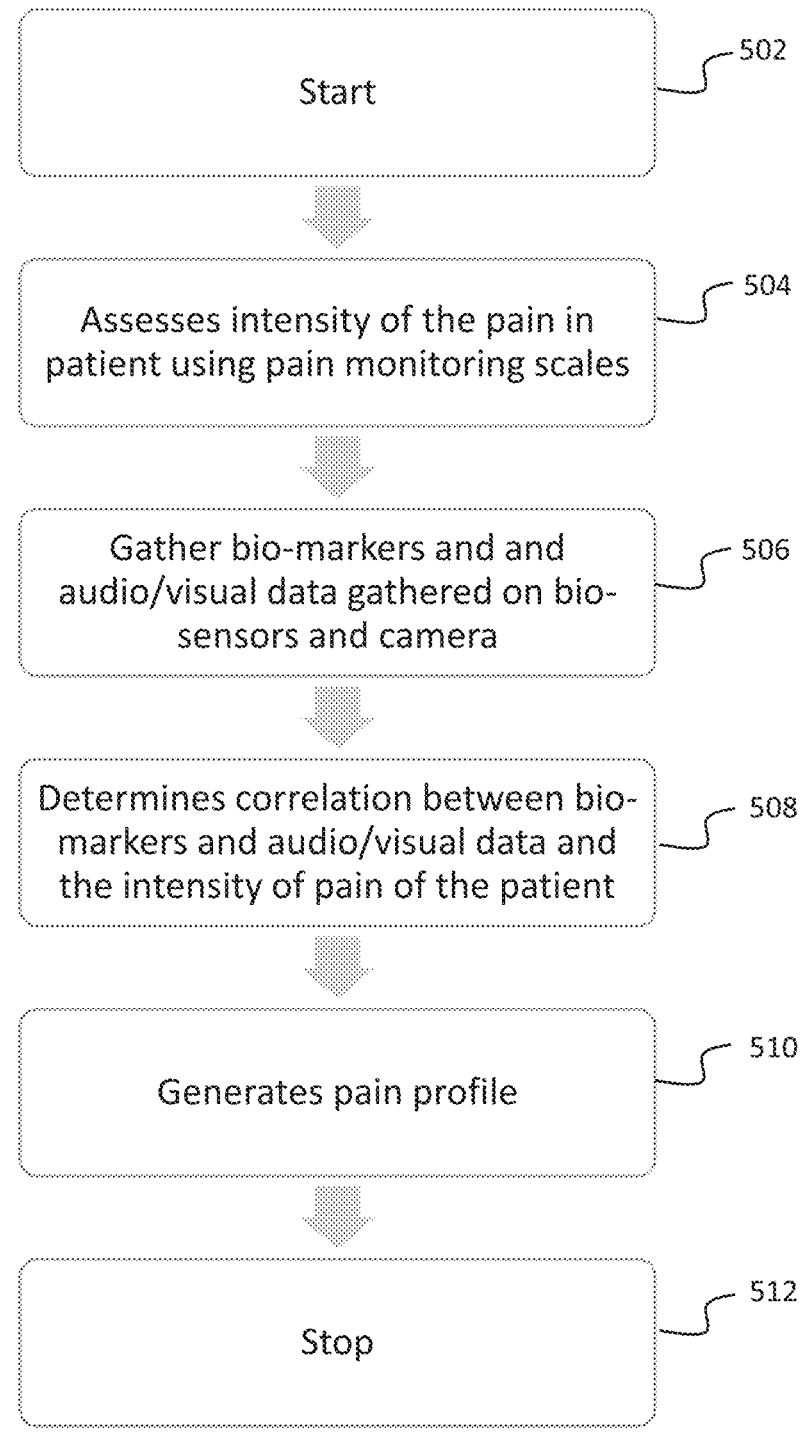
FIG. 5 depicts a flow chart for monitoring the intensity of the pain experienced by a patient in accordance with various embodiments of the present disclosure.

As illustrated in FIG. 5 a flow chart 500 for monitoring the intensity of the pain experienced by the patient, in accordance with the various embodiments of the present disclosure. The flow chart initiates at step 502. Following step 502, at step 504, the diagnostic application 410 assesses the intensity of the pain of each of the patients on one or more pain monitoring scales. At step 506, the plurality of bio-sensors and cameras gather the one or more bio-markers associated with the patient and take images and sound data from the patient using the one or more bio-markers and/or the audio and/or visual data gathered from camera. At step 508, the diagnostic application 410 combines the one or more physiologic, bio-markers, and the audio and visual data to determine an intensity of pain estimate. At step 510, the presentation application 412 generates a pain profile of the patient. The flow chart terminates at step 512.

Figure 6:
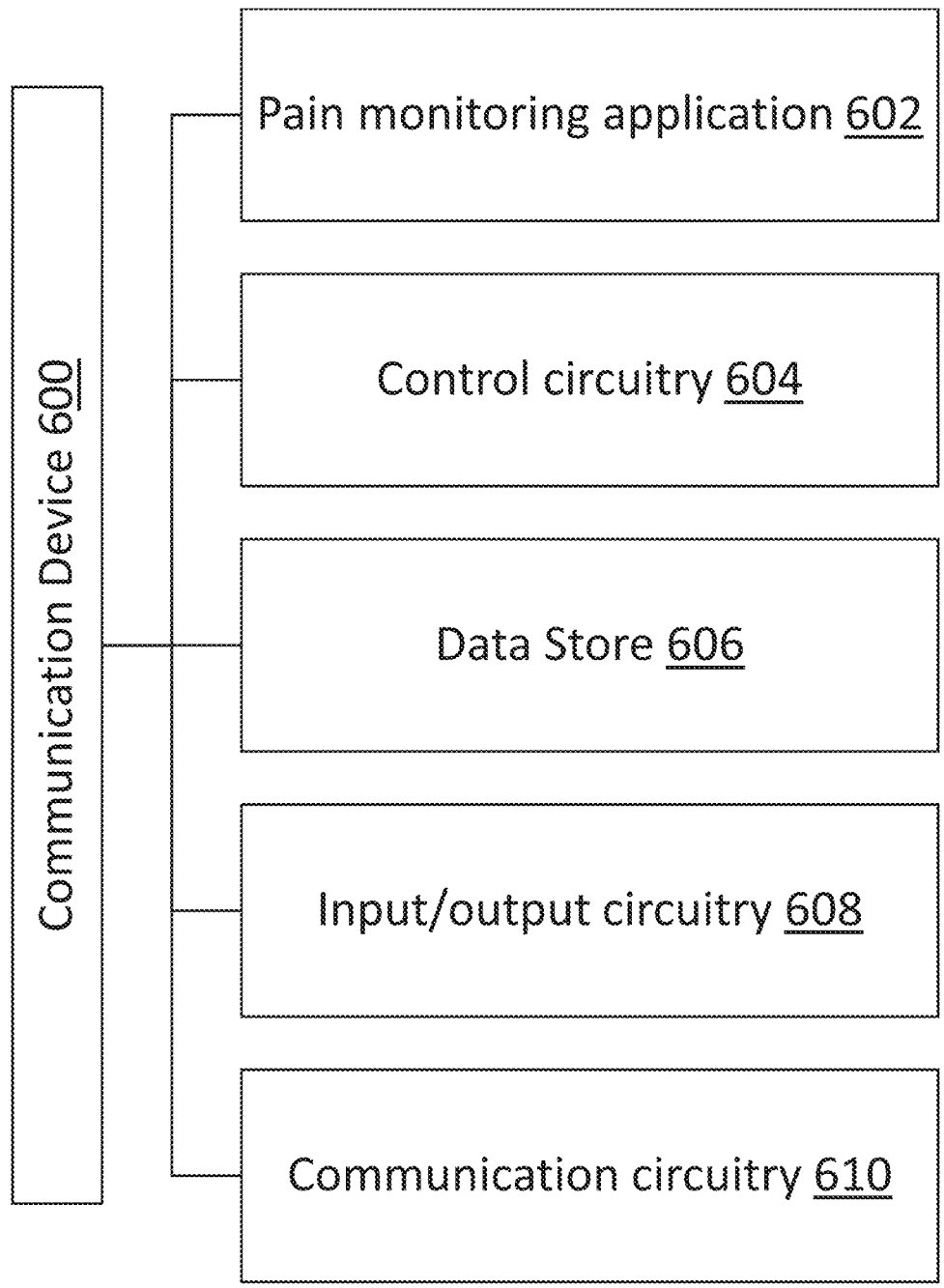
FIG. 6 depicts a block diagram of a communication device, in accordance with various embodiments of the present disclosure.

FIG. 6 illustrates a block diagram of a communication device 600, in accordance with various embodiments of the present disclosure. As stated above, in an embodiment, the communication device 600 enables the hosting of the pain monitoring application 602. The communication device 600 includes a control circuitry 604, a data store 606, input/output circuitry 608 and communication circuitry 610. The communication device 600 includes any suitable type of portable electronic device. Examples of the communication device 600 include but may not be limited to a personal e-mail device (e.g., a Blackberry™ made available by Research in Motion of Waterloo, Ontario), a personal data assistant ("PDA"), a cellular telephone, a Smartphone, a handheld gaming device, a digital camera, a laptop computer, a wearable device, and a tablet computer. In another embodiment of the present innovation, the communication device 600 can be a desktop computer.

The control circuitry 604 includes any processing circuitry or processor operative to control the operations and performance of the communication device 600. For example, the control circuitry 604 may be used to run operating system applications, firmware applications, media playback applications, media editing applications, or any other application. In an embodiment, the control circuitry 604 drives a display and process inputs received from a user interface.

The data store 606 includes one or more storage mediums including a hard-drive, solid state drive, flash memory, permanent memory such as ROM, any other suitable type of storage component, or any combination thereof. The data store 606 may store, for example, media data (e.g., audio and video files), application data (e.g., for implementing functions on the communication device 600).

The I/O circuitry 608 may be operative to convert (and encode/decode, if necessary) analog signals and other signals into digital data. In an embodiment, the I/O circuitry 608 may also convert digital data into any other type of signal, and vice-versa. For example, the I/O circuitry 608 may receive and convert physical contact inputs (e.g., from a multi-touch screen), physical movements (e.g., from a mouse or sensor), analog audio signals (e.g., from a microphone), digital video data (e.g., from a camera), or any other input. The digital data may be provided to and received from the control circuitry 604, the data store 606, or any other component of the communication device 600.

It may be noted that the I/O circuitry 608 is illustrated in FIG. 6 as a single component of the communication device 600; however, those skilled in the art would appreciate that several instances of the I/O circuitry 608 may be included in the communication device 600.

The communication device 600 may include any suitable interface or component for allowing a user to provide inputs to the I/O circuitry 608. The communication device 600 may include any suitable input mechanism. Examples of the input mechanism include but may not be limited to a button, keypad, dial, a click wheel, and a touch screen. In an embodiment, the communication device 600 may include a capacitive sensing mechanism, or a multi-touch capacitive sensing mechanism.

In an embodiment, the communication device 600 may include specialized output circuitry associated with output devices such as, for example, one or more audio outputs. The audio output may include one or more speakers built into the communication device 600, or an audio component that may be remotely coupled to the communication device 600.

The one or more speakers can be mono speakers, stereo speakers, or a combination of both. The audio component can be a headset, headphones or ear buds that may be coupled to communications device with a wire or wirelessly.

In an embodiment, the I/O circuitry 608 may include display circuitry for providing a display visible to the user. For example, the display circuitry may include a screen (e.g., an LCD screen) that is incorporated in the communication device 600.

The display circuitry may include a movable display or a projecting system for providing a display of content on a surface remote from the communication device 600 (e.g., a video projector). In an embodiment, the display circuitry may include a coder/decoder to convert digital media data into analog signals. For example, the display circuitry may include video Codecs, audio Codecs, or any other suitable type of Codec.

The display circuitry may include display driver circuitry, circuitry for driving display drivers or both. The display circuitry may be operative to display content. The display content can include media playback information, application screens for applications implemented on the electronic device, information regarding ongoing communications operations, information regarding incoming communications requests, or device operation screens under the direction of the control circuitry 504. Alternatively, the display circuitry may be operative to provide instructions to a remote display.

In addition, the communication device 600 includes the communications circuitry 610. The communications circuitry 610 may include any suitable communications circuitry operative to connect to a communications network and to transmit communications (e.g., voice or data) from the communication device 600 to other devices within the communications network. The communications circuitry 610 may be operative to interface with the communications network using any suitable communications protocol. Examples of the communications protocol include but may not be limited to Wi-Fi, Bluetooth®, radio frequency systems, infrared, LTE, GSM, GSM plus EDGE, CDMA, and quadband.

In an embodiment, the communications circuitry 610 may be operative to create a communications network using any suitable communications protocol. For example, the communications circuitry 610 may create a short-range communications network using a short-range communications protocol to connect to other devices. For example, the communications circuitry 610 may be operative to create a local communications network using the Bluetooth,® protocol to couple the communication device 600 with a Bluetooth,® headset.

It may be noted that the computing device is shown to have only one communication operation; however, those skilled in the art would appreciate that the communication device 600 may include one more instance of the communications circuitry 610 for simultaneously performing several communications operations using different communications networks. For example, the communication device 600 may include a first instance of the communications circuitry 610 for communicating over a cellular network, and a second instance of the communications circuitry 610 for communicating over Wi-Fi or using Bluetooth®.

In an embodiment, the same instance of the communications circuitry 610 may be operative to provide for communications over several communications networks. In an embodiment, the communication device 600 may be coupled a host device for data transfers, synching the communications device, software or firmware updates, providing performance information to a remote source (e.g., providing riding characteristics to a remote server) or performing any other suitable operation that may require the communication device 600 to be coupled to a host device. Several computing devices may be coupled to a single host device using the host device as a server. Alternatively, or additionally, the communication device 600 may be coupled to several host devices (e.g., for each of the plurality of the host devices to serve as a backup for data stored in the communication device 600).

Example 4

In an embodiment of the present disclosure, the method of assessing pain takes place over two stages: training the system; and deploying the system. In the training stage, the pain classifier or detector is trained using digital videos or datasets.

The digital videos have either pain expression from a patient or no-pain expression. The caregiver enters a label for each video and classifies it as pain or no-pain. Using these labeled videos, a classifier, or pain detector, is trained to recognize the pattern of pain videos and no-pain videos and distinguish between them.

Numerical values are extracted from these videos to aid in training the machine learning classifiers (e.g., distance between upper and lower lips during crying and no-crying). Using these features, the classifier, or pain detector, is built. In the system there is a classifier, or pain detector, for each pain indicator, namely pain classifier for the facial expressions, pain classifier for the patient's body movement. There is also a fusion classifier that fuses all the indicators and provides a final label.

In the second, deployment stage, the trained classifier, or pain detector, is used. The classifier receives input in the form of a new instance or frame, and the trained classifier provides a label to this frame as pain or no-pain. This label, or alert, is then sent to an alert component, which may be a display on a caregiver's workstation via an electronic signal such as WiFi or a local network.

The pain detector can be applied in each frame or each second to obtain a real-time pain assessment of the patient. If the caregiver wants to receive an assessment, the caregiver can receive an assessment every one second, or at any desired time interval, such as 10 seconds or 1 minute. The caregiver can also change the configuration of the classifier to run for all indicators (fused pain classification) or run the classifier for specific pain indicators (e.g., facial expression).

The system is also able to save the labels of previous frames so the caregiver can look at the history of pain experienced by the patient when the caregiver needs to. Although the deployment stage uses an already trained classifier, the trained classifiers can be re-trained or fine-tuned as needed. For example, the trained classifier can be retrained or fine-tuned using a dataset of older pediatric patients, such as 3 (three) months old to 1 (one) year old rather than newborn infants or premature infants. After fine-tuning the classifier is redeployed as described above.

REFERENCES

[1] Y. Abdulaziz and S. M. S. Ahmad. Infant cry recognition system: A comparison of system performance based on mel frequency and linear prediction cepstral coefficients. In 2010 International Conference on Information Retrieval Knowledge Management (CAMP), pages 260-263, March 2010.

[2] Kanwaljeet J S Anand, Bonnie J Stevens, and Patrick J McGrath. Pain in neonates and infants. Elsevier Health Sciences, 2007.

[3] K J S Anand and Frank M Scalzo. Can adverse neonatal experiences alter brain development and subsequent behavior? Neonatology, 77(2):69-82, 2000.

[4] Dusica Bajic, Kathryn G Commons, and Sulpicio G Soriano. Morphine enhanced apoptosis in selective brain regions of neonatal rats. International Journal of Developmental Neuroscience, 31(4):258-266, 2013.

[5] Yaniv Bar, Idit Diamant, Lior Wolf, and Hayit Greenspan. Deep learning with non-medical training used for chest pathology identification. In Proc. SPIE, volume 9414, page 94140V, 2015.

[6] Sandra E. Barajas-Montiel and Carlos A. Reyes-García. Fuzzy Support Vector Machines for Automatic Infant Cry Recognition, pages 876-881. Springer Berlin Heidelberg, Berlin, Heidelberg, 2006.

[7] Carlo Valerio Bellieni. Pain assessment in human fetus and infants. The AAPS journal, 14(3):456-461, 2012.

[8] Adnan T Bhutta and K J S Anand. Vulnerability of the developing brain. Clinics in perinatology, 29(3):357-372, 2002.

[9] Adnan T Bhutta, Cynthia Rovnaghi, Pippa M Simpson, Jeffrey M Gossett, Frank M Scalzo, and K J S Anand. Interactions of inflammatory pain and morphine in infant rats: long-term behavioral effects. Physiology & behavior, 73(1):51-58, 2001.

[10] Sheryl Brahnam, Loris Nanni, and Randall Sexton. Introduction to Neonatal Facial Pain Detection Using Common and Advanced Face Classification Techniques, pages 225-253. Springer Berlin Heidelberg, Berlin, Heidelberg, 2007.

[11] Susanne Brummelte, Ruth E Grunau, Vann Chau, Kenneth J Poskitt, Rollin Brant, Jillian Vinall, Ayala Gover, Anne R Synnes, and Steven P Miller. Procedural pain and brain development in premature newborns. Annals of neurology, 71(3):385-396, 2012.

[12] Adrienne Stith Butler, Richard E Behrman, et al. Preterm birth: causes, consequences, and prevention. National Academies Press, 2007.

[13] Luigi Celona and Luca Manoni. Neonatal facial pain assessment combining hand-crafted and deep features. In International Conference on Image Analysis and Processing, pages 197-204. Springer, 2017.

[14] Stuart W G Derbyshire. Gender, pain, and the brain. Pain Clinical Updates, 16(3):1-4, 2008.

[15] Papa M Faye, Julien De Jonckheere, Regis Logier, Eliane Kuissi, Mathieu Jeanne, Thameur Rakza, and Laurent Storme. Newborn infant pain assessment using heart rate variability analysis. The Clinical journal of pain, 26(9):777-782, 2010.

[16] Tiffany Field. Preterm newborn pain research review. Infant Behavior and Development, 49:141-150, 2017.

[17] E. Fotiadou, S. Zinger, W. E. Tjon a Ten, S. Bambang Oetomo, and P. H. N de With. Video-based facial discomfort analysis for infants, 2014.

[18] Barbara F. Fuller and Yoshiyuki Horii. Spectral energy distribution in four types of infant vocalizations. Journal of Communication Disorders, 21(3):251-261, 1988.

[19] RE Grunau. Self-regulation and behavior in preterm children: effects of early pain. Progress in pain research and management, 26:23-56, 2003.

[20] Ruth E Grunau, Liisa Holsti, and Jeroen W B Peters. Long-term consequences of pain in human neonates. In Seminars in Fetal and Neonatal Medicine, volume 11, pages 268-275. Elsevier, 2006.

[21] Ruth E Grunau, Mai Thanh Tu, Michael F Whitfield, Tim F Oberlander, Joanne Weinberg, Wayne Yu, Paul Thiessen, Gisela Gosse, and David Scheifele. Cortisol, behavior, and heart rate reactivity to immunization pain at 4 months corrected age in infants born very preterm. The Clinical journal of pain, 26(8):698, 2010.

[22] Ruth V E Grunau and Kenneth D Craig. Pain expression in neonates: facial action and cry. Pain, 28(3):395-410, 1987.

[23] Shuxian Hu, Wen S Sheng, James R Lokensgard, and Phillip K Peterson. Morphine induces apoptosis of human microglia and neurons. Neuropharmacology, 42(6):829-836, 2002.

[24] László A Jeni, Jeffrey F Cohn, and Takeo Kanade. Dense 3d face alignment from 2d videos in real-time. In Automatic Face and Gesture Recognition (FG), 2015 11th IEEE International Conference and Workshops on, volume 1, pages 1-8. IEEE, 2015.

[25] Muhammad Naufal Mansor and Mohd Nazri Rejab. A computational model of the infant pain impressions with gaussian and nearest mean classifier. In Control System, Computing and Engineering (ICCSCE), 2013 IEEE International Conference on, pages 249-253. IEEE, 2013.

[26] C. Celeste Johnston Bonnie J. Stevens Marco Petroni, Alfred S. Malowany. Identification of pain from infant cry vocalizations using artificial neural networks (anns), 1995.

[27] Margo McCaffery. Nursing practice theories related to cognition, bodily pain, and man-environment interactions. University of California Print. Office, 1968.

[28] Carly Miller and Sarah E Newton. Pain perception and expression: the influence of gender, personal self-efficacy, and lifespan socialization. Pain Management Nursing, 7(4):148-152, 2006.

[29] Loris Nanni, Sheryl Brahnam, and Alessandra Lumini. A local approach based on a local binary patterns variant texture descriptor for classifying pain states. Expert Systems with Applications, 37(12):7888-7894, 2010.

[30] American Academy of Pediatrics, Fetus, Newborn Committee, et al. Prevention and management of pain in the neonate: an update. Pediatrics, 118(5):2231-2241, 2006.

[31] Harriet Oster. Baby facs: Facial action coding system for infants and young children. Unpublished monograph and coding manual. New York University, 2006.

[32] Chih-Yun Pai. Automatic pain assessment from infants crying sounds. 2016.

[33] P. Pal, A. N. Iyer, and R. E. Yantorno. Emotion detection from infant facial expressions and cries. In 2006 IEEE International Conference on Acoustics Speech and Signal Processing Proceedings, volume 2, pages II-II, May 2006.

[34] Jeroen W B Peters, Hans M Koot, Ruth E Grunau, Josien de Boer, Marieke J van Druenen, Dick Tibboel, and Hugo J Duivenvoorden. Neonatal facial coding system for assessing postoperative pain in infants: item reduction is valid and feasible. The Clinical journal of pain, 19(6): 353-363, 2003.

[35] Rebecca R Pillai Riddell, Melanie A Badali, and Kenneth D Craig. Parental judgments of infant pain: Importance of perceived cognitive abilities, behavioural cues and contextual cues. Pain Research and Management, 9(2):73-80, 2004.

[36] Sinno H P Simons, Monique van Dijk, Kanwaljeet S Anand, Daniella Roofthooft, Richard A van Lingen, and Dick Tibboel. Do we still hurt newborn babies?: A prospective study of procedural pain and analgesia in neonates. Archives of pediatrics & adolescent medicine, 157(11):1058-1064, 2003.

[37] Rebeccah Slater, Anne Cantarella, Shiromi Gallella, Alan Worley, Stewart Boyd, Judith Meek, and Maria Fitzgerald. Cortical pain responses in human infants. Journal of Neuroscience, 26(14):3662-3666, 2006.

[38] Beatriz Oliveira Valeri and Maria Beatriz Martins Linhares. Pain in preterm infants: Effects of sex, gestational age, and neonatal illness severity. Psychology & Neuroscience, 5(1):11, 2012.

[39] Ramu Reddy Vempada, B Siva Ayyappa Kumar, and K Sreenivasa Rao. Characterization of infant cries using spectral and prosodic features. In Communications (NCC), 2012 National Conference on, pages 1-5. IEEE, 2012.

[40] Jillian Vinall, Steven P Miller, Vann Chau, Susanne Brummelte, Anne R Synnes, and Ruth E Grunau. Neonatal pain in relation to postnatal growth in infants born very preterm. Pain, 153(7):1374-1381, 2012.

[41] Terri Voepel-Lewis, Sandy Merkel, Alan R Tait, Agnieszka Trzcinka, and Shobha Malviya. The reliability and validity of the face, legs, activity, cry, consolability observational tool as a measure of pain in children with cognitive impairment. Anesthesia & Analgesia, 95(5): 1224-1229, 2002.

[42] Betty R Vohr, Linda L Wright, Anna M Dusick, Lisa Mele, Joel Verter, Jean J Steichen, Neal P Simon, Dee C Wilson, Sue Broyles, Charles R Bauer, et al. Neurodevelopmental and functional outcomes of extremely low birth weight infants in the national institute of child health and human development neonatal research network, 1993-1994. Pediatrics, 105(6):1216-1226, 2000.

[43] Suellen M Walker. Translational studies identify longterm impact of prior neonatal pain experience. Pain, 158:S29-S42, 2017.

[44] Ghada Zamzami, Gabriel Ruiz, Dmitry Goldgof, Rangachar Kasturi, Yu Sun, and Terri Ashmeade. Pain assessment in infants: Towards spotting pain expression based on infants' facial strain. In Automatic Face and Gesture Recognition (FG), 2015 11th IEEE International Conference and Workshops on, volume 5, pages 1-5. IEEE, 2015.

[45] Ghada Zamzami, Rangachar Kasturi, Dmitry Goldgof, Ruicong Zhi, Terri Ashmeade, and Yu Sun. A review of automated pain assessment in infants: Features, classification tasks, and databases. IEEE Reviews in Biomedical Engineering, 2017.

[46] Ghada Zamzami, Chih-Yun Pai, Dmitry Goldgof, Rangachar Kasturi, Terri Ashmeade, and Yu Sun. An approach for automated multimodal analysis of infants' pain. In Pattern Recognition (ICPR), 2016 $23^{rd}$ International Conference on, pages 4148-4153. IEEE, 2016.

[47] Ghada Zamzami, Chih-Yun Pai, Dmitry Goldgof, Rangachar Kasturi, Yu Sun, and Terri Ashmeade. Automated pain assessment in neonates. In Scandinavian Conference on Image Analysis, pages 350-361. Springer, 2017.

[48] Jill G Zwicker, Steven P Miller, Ruth E Grunau, Vann Chau, Rollin Brant, Colin Studholme, Mengyuan Liu, Anne Synnes, Kenneth J Poskitt, Mikaela L Stiver, et al. Smaller cerebellar growth and poorer neurodevelopmental outcomes in very preterm infants exposed to neonatal morphine. The Journal of pediatrics, 172:81-87, 2016.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The advantages set forth above, and those made apparent from the foregoing description, are efficiently attained. While the disclosure is susceptible to various modifications and implementation in alternative forms, specific embodiments have been shown by way of non-limiting example in the drawings and have been described in detail herein. Since certain changes may be made in the above construction without departing from the scope of the instant application, it is intended that all matters contained in the foregoing description or shown in the accompanying drawings shall be interpreted as illustrative and not in a limiting sense.

The disclosure is not intended to be limited to the particular forms disclosed. Rather, the disclosure is to cover all modifications, equivalents, and alternatives falling within the scope of the disclosure as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

It is also to be understood that the following claims are intended to cover all of the generic and specific features of the invention herein described, and all statements of the scope of the invention that, as a matter of language, might be said to fall therebetween.

What is claimed is:

1. A pain assessment system configured to alert a caregiver when pain is detected in a patient, the system comprising:
   a camera configured to capture digital images of facial expressions of the patient and digital images of the patient's body;
   a pain determination application configured to receive one or more digital images of facial expression of the patient and of the patient's body from the camera;
      wherein the pain determination application automatically registers a plurality of anatomical landmark points on the one or more digital images of the facial expressions, and automatically tracks coordinates of each of the plurality of anatomical landmark points;
      wherein the pain determination application creates a region of interest of the one or more digital images of the patient's body;
      wherein the pain determination application automatically tracks a location of each of the plurality of anatomical landmark points of the one or more digital images of facial expression to determine whether changes in relative locations of the plurality of anatomical landmark points have exceeded a predetermined threshold that indicates the patient is experiencing pain;
      wherein the pain determination application automatically tracks the region of interest on the one or more digital images of the patient's body to determine whether changes in the region of interest have exceeded a predetermined threshold that indicates the patient is experiencing pain;
   a medical device configured to gather physiological data from a patient through a plurality of bio-sensors;
   a contextual data gathering device, wherein the contextual data gathering device stores a pain monitoring scale data point and a contextual dataset of the patient and wherein the physiological data and the pain monitoring scale data point and contextual dataset of the patient are combined with the determination that the patient is in pain from the pain determination application to generate a multimodal pain assessment; and
   a pain alerting system adapted to automatically deliver the multimodal pain assessment to the caregiver.

2. The pain assessment system of claim 1, wherein the pain determination application creates the region of interest of the one or more digital images of the patient's body to monitor for body movements of the patient by creating a plurality of patches, half of which are body patches and the other half are non-body patches, wherein the plurality of patches is converted to a Luminance, Choma: Blue; Chroma: Red (YCbCr) color space and a Cb and Cr histograms of the plurality of patches is generated, wherein the normal distribution of the Cb histograms for the plurality of patches is generated, wherein the normal distribution of the Cr histograms for the plurality of patches is generated, wherein using the Cb and Cr histograms the one or more digital images of the patient's body is converted into a black and white binary image and wherein the black and white binary image is used to create the region of interest to monitor for body movements of the patient.

3. The pain assessment system of claim 1, wherein the generation of the multimodal pain assessment is done using either a feature-level method or a decision-level method.

4. The pain assessment system of claim 1, wherein the plurality of bio-sensors are adapted to be attached to various points on a body of the patient.

5. The pain assessment system of claim 1, wherein the plurality of bio-sensors comprise one or more of a finger-based pulse oximeter, an accelerometer, a respiration monitor, a 1-lead disposable electrocardiography (ECG) patch, a multiple lead ECG, an electroencephalography (EEG) sensor, and a muscle activity sensor.

6. The pain assessment system of claim 1, wherein the physiological data comprises one or more of heart rate (HR), heart rate variability (HRV), skin conductance, respiration information, blood pressure, photoplethysmography (PPG), oxygen saturation, single or multiple lead electrocardiography (ECG), electroencephalography (EEG), muscle activity (EMG), galvanic skin response (GSR), skin conductance, pulse wave transit time, atrial kick, BCG (Balistocardiogram), EOG (Electrooculography), Dispersion based ECG, Impedence cardiography, $VO_2$ max, $PaCO_2$, cardiac output, blood glucose, arterial blood gas, temperature, and urine output.

7. The pain assessment system of claim 1, wherein the pain monitoring scale data point is generated by the caregiver using a pain scale selected from the group consisting of, a visual analog scale (VAS), a verbal numerical rating scale (VNRS), a brief pain inventory (BPI), a verbal descriptor scale (VDS), a neonatal pain agitation and sedation scale (N-PASS), a pain assessment tool (PAT), a bernese pain scale for one or more neonates (BPSN), a Neonatal Infant Pain Scale (NIPS), a wong-baker scale, a face, legs, activity, crying, and consolability (FLACC) scale.

8. The pain assessment system of claim 1, wherein the contextual dataset includes a phenotypic dataset, a genotypic dataset, and a disposition of the patient;
wherein the phenotypic dataset includes gender and race;
wherein the genotypic dataset includes a genetic profile, and any genetic diseases; and
wherein the disposition of the patient includes the amount of sleep the patient has had, the last time the patient was fed, mood, and attention.

9. The pain assessment system of claim 1, wherein the contextual data gathering device collects experimental factors including duration of measurement of the intensity of the pain and location of each sensor of the plurality of bio-sensors on the body of the patient.

10. The pain assessment system of claim 1, wherein the camera captures facial expressions of the patient along with sounds, and body movement at recorded time period intervals of five (5), ten (10), and fifteen (15) seconds and wherein a tracker was applied to the facial expressions to obtain facial landmark points and face boundary points.

11. The pain assessment system of claim 10, wherein the facial expressions are extracted with strain-based and geometric-based extraction to extract pain-relevant features from the patient.

12. The pain assessment system of claim 1, wherein the camera captures audio data that is segmented into audio signal and divided into several Hamming windows of 32-millisecond that shifts every 16-millisecond and Hamming windows of 30-millisecond that shifts every 10-millisecond to minimize the signal discontinuities.

13. The pain assessment system of claim 1, wherein the physiological data is processed with a median filter to calculate several descriptive statistics for the physiological data across the pain or a no pain event.

14. A method for monitoring an intensity of pain experienced by a patient, the method comprising:
capturing digital images of facial expressions of the patient along with sounds, and digital images of the patient's body;
registering a plurality of anatomical landmark points on one or more digital images of facial expressions of the patient, and automatically tracking coordinates of each of the plurality of anatomical landmark points to determine whether changes in the coordinates of each of the plurality of anatomical landmark points have exceeded a predetermined threshold that indicates the patient is experiencing pain;
registering a region of interest on one or more digital images of the patient's body and automatically tracking the region of interest to determine whether changes in the region of interest have exceeded a predetermined threshold that indicates the patient is experiencing pain;
gathering physiological data of the patient from a plurality of bio-sensors;
gathering a contextual dataset of the patient, wherein the contextual dataset includes a phenotypic dataset, a genotypic dataset, and a disposition of the patient, wherein the phenotypic dataset includes gender and race, wherein the genotypic dataset includes a genetic profile, and any genetic diseases and wherein the disposition of the patient includes the amount of sleep the patient has had, the last time the patient was fed, mood, and attention;
storing a pain monitoring scale data point and the contextual data set of the patient at a contextual data gathering device;
combining the determination of whether the patient is experiencing pain with the physiological data of the patient, the pain monitoring scale data point and the contextual dataset of the patient into a multimodal pain profile of the patient; and
delivering the multimodal pain profile of the patient to a caregiver.

15. The method of claim 14, wherein the determination of whether the patient is experiencing pain is used to train a machine learning classifier.

16. The method of claim 15, wherein the machine learning classifier is selected from the group consisting of Naïve Bayes, Nearest Neighbors (kNN), Support Vector Machines (SVMs), and Random Forests (RF) classifiers.

17. A non-transitory computer readable storage media having computer-executable instructions, when executed by a processor for, monitoring and assessing an intensity of pain experienced by a patient, comprising:

capturing digital images of facial expressions of the patient along with sounds, and digital images of the patient's body;

registering a plurality of anatomical landmark points on one or more digital images of facial expressions of the patient, and automatically tracking coordinates of each of the plurality of anatomical landmark points to determine whether changes in the coordinates of each of the plurality of anatomical landmark points have exceeded a predetermined threshold that indicates the patient is experiencing pain;

registering a region of interest on one or more digital images of the patient's body and automatically tracking the region of interest to determine whether changes in the region of interest have exceeded a predetermined threshold that indicates the patient is experiencing pain;

gathering physiological data of the patient from a plurality of bio-sensors;

gathering a contextual dataset of the patient, wherein the contextual dataset includes a phenotypic dataset, a genotypic dataset, and a disposition of the patient, wherein the phenotypic dataset includes gender and race, wherein the genotypic dataset includes a genetic profile, and any genetic diseases and wherein the disposition of the patient includes the amount of sleep the patient has had, the last time the patient was fed, mood, and attention;

storing a pain monitoring scale data point and the contextual data set of the patient at a contextual data gathering device;

combining the determination of whether the patient is experiencing pain with the physiological data of the patient, the pain monitoring scale data point and the contextual dataset of the patient into a multimodal pain profile of the patient; and delivering the multimodal pain profile of the patient to a caregiver.

* * * * *